(12) United States Patent
Salo et al.

(10) Patent No.: US 7,742,815 B2
(45) Date of Patent: Jun. 22, 2010

(54) USING IMPLANTED SENSORS FOR FEEDBACK CONTROL OF IMPLANTED MEDICAL DEVICES

(75) Inventors: Rodney Salo, Fridley, MN (US); Abhijeet Chavan, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 632 days.

(21) Appl. No.: 11/223,398

(22) Filed: Sep. 9, 2005

(65) Prior Publication Data

US 2007/0060959 A1 Mar. 15, 2007

(51) Int. Cl.
*A61N 1/36* (2006.01)
(52) U.S. Cl. ........................................... 607/23
(58) Field of Classification Search .................. 607/23, 607/44
See application file for complete search history.

(56) References Cited

U.S. PATENT DOCUMENTS

| | | | |
|---|---|---|---|
| 3,310,885 | A | 3/1967 | Alderson |
| 3,320,946 | A | 5/1967 | Dethloff et al. |
| 3,536,836 | A | 10/1970 | Pfeiffer |
| 3,568,661 | A | 3/1971 | Franklin |
| 3,672,352 | A | 6/1972 | Summers |
| 3,692,027 | A | 9/1972 | Ellinwood |
| 3,757,770 | A | 9/1973 | Brayshaw et al. |
| 3,794,840 | A | 2/1974 | Scott |
| 3,943,915 | A | 3/1976 | Severson |
| 4,003,379 | A | 1/1977 | Ellinwood |
| 4,041,954 | A | 8/1977 | Ohara |
| 4,127,110 | A | 11/1978 | Bullara |
| 4,146,029 | A | 3/1979 | Ellinwood |
| 4,223,801 | A | 9/1980 | Carlson |
| 4,227,407 | A | 10/1980 | Drost |
| 4,237,900 | A | 12/1980 | Schulman et al. |

(Continued)

FOREIGN PATENT DOCUMENTS

EP 0897690 2/1999

(Continued)

OTHER PUBLICATIONS

International Search Report and Written Opinion of International Application No. PCT/US2006/034602, filed Sep. 6, 2006, both mailed Jan. 23, 2007.

(Continued)

*Primary Examiner*—Carl H. Layno
*Assistant Examiner*—Jon-Eric C. Morales
(74) *Attorney, Agent, or Firm*—Faegre & Benson LLP

(57) ABSTRACT

A system and method for administering a therapeutic treatment to the heart, includes a pressure sensor positioned in the pulmonary artery, an implantable medical device located remotely from the sensor, and communication means for communicating pressure data from the pressure sensor to the implantable medical device. The system includes a control module operatively coupled to the implantable medical device. The control module is adapted for comparing the pulmonary arterial pressure data to a pre-programmed value, adjusting an operating parameter of the implantable medical device based on the relationship of the pulmonary arterial pressure to the pre-programmed value, and repeating this process until the relationship between the pulmonary arterial pressure data and the pre-programmed value is such that no adjustment is necessary.

10 Claims, 11 Drawing Sheets

U.S. PATENT DOCUMENTS

| | | |
|---|---|---|
| 4,281,664 A | 8/1981 | Duggen |
| 4,360,019 A | 11/1982 | Portner et al. |
| 4,407,296 A | 10/1983 | Anderson |
| 4,450,527 A | 5/1984 | Sramek |
| 4,480,483 A | 11/1984 | McShane |
| 4,519,401 A | 5/1985 | Ko et al. |
| 4,541,431 A | 9/1985 | Ibrahim et al. |
| 4,543,955 A | 10/1985 | Schroeppel |
| 4,550,370 A | 10/1985 | Baker |
| 4,585,004 A | 4/1986 | Brownlee |
| 4,593,703 A | 6/1986 | Cosman |
| 4,600,855 A | 7/1986 | Strachan |
| 4,616,640 A | 10/1986 | Kaali et al. |
| 4,651,740 A | 3/1987 | Schroeppel |
| 4,653,508 A | 3/1987 | Cosman |
| 4,660,568 A | 4/1987 | Cosman |
| 4,676,255 A | 6/1987 | Cosman |
| 4,677,985 A | 7/1987 | Bro et al. |
| 4,680,957 A | 7/1987 | Dodd |
| 4,686,987 A | 8/1987 | Salo et al. |
| 4,697,595 A | 10/1987 | Breyer et al. |
| 4,719,921 A * | 1/1988 | Chirife .................... 607/23 |
| 4,768,176 A | 8/1988 | Kehr et al. |
| 4,768,177 A | 8/1988 | Kehr et al. |
| 4,781,715 A | 11/1988 | Wurzel |
| 4,791,936 A | 12/1988 | Snell et al. |
| 4,793,825 A | 12/1988 | Benjamin et al. |
| 4,809,697 A | 3/1989 | Causey, III et al. |
| 4,845,503 A | 7/1989 | Adam et al. |
| 4,846,191 A | 7/1989 | Brockway et al. |
| 4,854,327 A | 8/1989 | Kunig |
| 4,899,752 A | 2/1990 | Cohen |
| 4,909,259 A | 3/1990 | Tehrani |
| 4,945,914 A | 8/1990 | Allen |
| 4,967,749 A | 11/1990 | Cohen |
| 4,986,270 A | 1/1991 | Cohen |
| 4,991,579 A | 2/1991 | Allen |
| 4,995,068 A | 2/1991 | Chou et al. |
| 4,995,398 A | 2/1991 | Turnidge |
| 5,003,976 A | 4/1991 | Alt |
| 5,024,224 A | 6/1991 | Engebretson |
| 5,025,795 A | 6/1991 | Kunig |
| 5,029,582 A | 7/1991 | Lekholm |
| 5,040,536 A | 8/1991 | Riff |
| 5,040,538 A | 8/1991 | Mortazavi |
| 5,113,859 A | 5/1992 | Funke |
| 5,154,171 A | 10/1992 | Chirife |
| 5,161,536 A | 11/1992 | Vilkomerson et al. |
| 5,163,429 A | 11/1992 | Cohen |
| 5,178,151 A | 1/1993 | Sackner |
| 5,178,153 A | 1/1993 | Einzig |
| 5,183,051 A | 2/1993 | Kraidin et al. |
| 5,190,035 A | 3/1993 | Salo et al. |
| 5,199,428 A | 4/1993 | Obel et al. |
| 5,200,891 A | 4/1993 | Kehr et al. |
| 5,213,098 A | 5/1993 | Bennett et al. |
| 5,246,008 A | 9/1993 | Mueller |
| 5,265,615 A | 11/1993 | Frank et al. |
| 5,267,174 A | 11/1993 | Kaufman et al. |
| 5,277,191 A | 1/1994 | Hughes |
| 5,279,309 A | 1/1994 | Taylor et al. |
| 5,279,607 A | 1/1994 | Schentag et al. |
| 5,289,821 A | 3/1994 | Swartz |
| 5,300,092 A | 4/1994 | Schaldach |
| 5,314,457 A | 5/1994 | Jeutter et al. |
| 5,329,459 A | 7/1994 | Kaufman et al. |
| 5,330,505 A | 7/1994 | Cohen |
| 5,339,051 A | 8/1994 | Koehler et al. |
| 5,368,040 A | 11/1994 | Carney |
| 5,375,603 A | 12/1994 | Feiler |
| 5,394,457 A | 2/1995 | Leibinger et al. |
| 5,397,329 A | 3/1995 | Allen |
| 5,400,793 A | 3/1995 | Wesseling |
| 5,411,535 A | 5/1995 | Fujii et al. |
| 5,411,551 A | 5/1995 | Winston et al. |
| 5,417,717 A | 5/1995 | Salo et al. |
| 5,423,323 A | 6/1995 | Orth |
| 5,423,334 A | 6/1995 | Jordan |
| 5,438,990 A | 8/1995 | Wahlstrand et al. |
| 5,445,608 A | 8/1995 | Chen et al. |
| 5,454,838 A | 10/1995 | Vallana et al. |
| 5,469,859 A | 11/1995 | Tsoglin et al. |
| 5,476,488 A | 12/1995 | Morgan et al. |
| 5,488,954 A | 2/1996 | Sleva et al. |
| 5,490,962 A | 2/1996 | Cima et al. |
| 5,509,424 A | 4/1996 | Al Ali |
| 5,528,067 A | 6/1996 | Farb |
| 5,535,752 A | 7/1996 | Halperin et al. |
| 5,558,091 A | 9/1996 | Acker et al. |
| 5,562,714 A | 10/1996 | Grevious |
| 5,564,434 A | 10/1996 | Halperin et al. |
| 5,571,152 A | 11/1996 | Chen et al. |
| 5,604,531 A | 2/1997 | Iddan et al. |
| 5,619,997 A | 4/1997 | Kaplan |
| 5,626,630 A | 5/1997 | Markowitz et al. |
| 5,628,782 A | 5/1997 | Myers |
| 5,642,731 A | 7/1997 | Kehr |
| 5,643,327 A | 7/1997 | Dawson et al. |
| 5,647,369 A | 7/1997 | Petrucelli et al. |
| 5,656,428 A | 8/1997 | McAllister et al. |
| 5,704,352 A | 1/1998 | Tremblay et al. |
| 5,705,753 A | 1/1998 | Hastings et al. |
| 5,728,281 A | 3/1998 | Holmstrom et al. |
| 5,729,129 A | 3/1998 | Acker |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,749,909 A | 5/1998 | Schroeppel et al. |
| 5,752,235 A | 5/1998 | Kehr et al. |
| 5,752,976 A | 5/1998 | Duffin et al. |
| 5,755,766 A | 5/1998 | Chastain et al. |
| 5,769,877 A | 6/1998 | Barreras, Sr. |
| 5,776,324 A | 7/1998 | Usala |
| 5,792,195 A | 8/1998 | Carlson et al. |
| 5,796,827 A | 8/1998 | Coppersmith et al. |
| 5,797,395 A | 8/1998 | Martin |
| 5,800,478 A | 9/1998 | Chen et al. |
| 5,807,258 A | 9/1998 | Cimochowski et al. |
| 5,807,395 A | 9/1998 | Mulier et al. |
| 5,807,397 A | 9/1998 | Barreras |
| 5,810,009 A | 9/1998 | Mine et al. |
| 5,810,735 A | 9/1998 | Halperin et al. |
| 5,832,924 A | 11/1998 | Archibald et al. |
| 5,833,603 A | 11/1998 | Kovacs et al. |
| 5,835,455 A | 11/1998 | Hanson et al. |
| 5,836,300 A | 11/1998 | Mault |
| 5,843,135 A | 12/1998 | Weijand et al. |
| 5,855,609 A | 1/1999 | Knapp |
| 5,856,722 A | 1/1999 | Haronian et al. |
| 5,868,673 A | 2/1999 | Vesely |
| 5,873,835 A | 2/1999 | Hastings et al. |
| 5,886,267 A | 3/1999 | Ortiz |
| 5,891,180 A | 4/1999 | Greeninger et al. |
| 5,904,708 A | 5/1999 | Goedeke et al. |
| 5,911,685 A | 6/1999 | Siess et al. |
| 5,919,221 A | 7/1999 | Miesel |
| 5,941,249 A | 8/1999 | Maynard |
| 5,954,641 A | 9/1999 | Kehr et al. |
| 5,957,950 A | 9/1999 | Mockros et al. |
| 5,967,986 A | 10/1999 | Cimochowski et al. |
| 5,979,898 A | 11/1999 | Pan |
| 6,002,963 A | 12/1999 | Mouchawar et al. |
| 6,023,641 A | 2/2000 | Thompson |
| 6,024,704 A | 2/2000 | Meador et al. |

| Patent No. | Kind | Date | Inventor |
|---|---|---|---|
| 6,050,951 | A | 4/2000 | Friedman et al. |
| 6,053,873 | A | 4/2000 | Govari et al. |
| 6,083,248 | A | 7/2000 | Thompson |
| 6,112,116 | A | 8/2000 | Fischell et al. |
| 6,123,861 | A | 9/2000 | Santini, Jr. et al. |
| 6,140,740 | A | 10/2000 | Porat et al. |
| 6,141,588 | A | 10/2000 | Cox et al. |
| 6,152,885 | A | 11/2000 | Taepke |
| 6,155,267 | A | 12/2000 | Nelson |
| 6,161,032 | A | 12/2000 | Acker |
| 6,162,238 | A | 12/2000 | Kaplan et al. |
| 6,171,252 | B1 | 1/2001 | Roberts |
| 6,179,767 | B1 | 1/2001 | Ziegler et al. |
| 6,185,452 | B1 | 2/2001 | Schulman et al. |
| 6,198,965 | B1 | 3/2001 | Penner et al. |
| 6,200,265 | B1 | 3/2001 | Walsh et al. |
| 6,234,973 | B1 | 5/2001 | Meador et al. |
| 6,236,889 | B1 | 5/2001 | Soykan et al. |
| 6,237,398 | B1 | 5/2001 | Porat et al. |
| 6,239,724 | B1 | 5/2001 | Doron et al. |
| 6,248,080 | B1 | 6/2001 | Miesel et al. |
| 6,256,538 | B1 | 7/2001 | Ekwall |
| 6,266,567 | B1 | 7/2001 | Ishikawa et al. |
| 6,273,904 | B1 | 8/2001 | Chen et al. |
| 6,277,078 | B1 | 8/2001 | Porat et al. |
| 6,278,894 | B1 | 8/2001 | Salo et al. |
| 6,305,381 | B1 | 10/2001 | Weijand et al. |
| 6,308,099 | B1 | 10/2001 | Fox et al. |
| 6,314,323 | B1 | 11/2001 | Ekwall |
| 6,330,957 | B1 | 12/2001 | Bell-Greenstreet |
| 6,331,163 | B1 | 12/2001 | Kaplan |
| 6,368,275 | B1 | 4/2002 | Sliwa et al. |
| 6,397,661 | B1 | 6/2002 | Grimes et al. |
| 6,409,674 | B1 | 6/2002 | Brockway et al. |
| 6,409,675 | B1 | 6/2002 | Turcott |
| 6,411,850 | B1 | 6/2002 | Kay et al. |
| 6,416,474 | B1 | 7/2002 | Penner et al. |
| 6,431,175 | B1 | 8/2002 | Penner et al. |
| 6,432,050 | B1 | 8/2002 | Porat et al. |
| 6,438,408 | B1 | 8/2002 | Mulligan et al. |
| 6,441,747 | B1 | 8/2002 | Khair et al. |
| 6,442,413 | B1 | 8/2002 | Silver |
| 6,445,953 | B1 | 9/2002 | Bulkes et al. |
| 6,456,883 | B1 | 9/2002 | Torgerson et al. |
| 6,471,645 | B1 | 10/2002 | Warkentin et al. |
| 6,472,991 | B1 | 10/2002 | Schulman et al. |
| 6,475,170 | B1 | 11/2002 | Doron et al. |
| 6,486,588 | B2 | 11/2002 | Doron et al. |
| 6,504,286 | B1 | 1/2003 | Porat et al. |
| 6,522,914 | B1 | 2/2003 | Huvelle et al. |
| 6,567,700 | B1 | 5/2003 | Turcott et al. |
| 6,574,510 | B2 | 6/2003 | Von Arx et al. |
| 6,580,946 | B2 | 6/2003 | Struble |
| 6,604,000 | B2 | 8/2003 | Lu |
| 6,607,485 | B2 | 8/2003 | Bardy |
| 6,609,023 | B1 | 8/2003 | Fischell et al. |
| 6,615,083 | B2 | 9/2003 | Kupper |
| 6,622,049 | B2 | 9/2003 | Penner et al. |
| 6,628,989 | B1 | 9/2003 | Penner et al. |
| 6,638,231 | B2 | 10/2003 | Govari et al. |
| 6,644,322 | B2 | 11/2003 | Webb |
| 6,654,638 | B1 | 11/2003 | Sweeney |
| 6,675,049 | B2 | 1/2004 | Thompson et al. |
| 6,699,186 | B1 | 3/2004 | Wolinsky et al. |
| 6,702,847 | B2 | 3/2004 | DiCarlo |
| 6,708,061 | B2 | 3/2004 | Salo et al. |
| 6,708,065 | B2 | 3/2004 | Von Arx et al. |
| 6,712,772 | B2 | 3/2004 | Cohen et al. |
| 6,720,709 | B2 | 4/2004 | Porat et al. |
| 6,720,887 | B1 | 4/2004 | Zunti |
| 6,733,447 | B2 | 5/2004 | Lai et al. |
| 6,738,667 | B2 | 5/2004 | Deno et al. |
| 6,738,671 | B2 | 5/2004 | Christophersom et al. |
| 6,743,173 | B2 | 6/2004 | Penner et al. |
| 6,758,822 | B2 | 7/2004 | Romano |
| 6,764,446 | B2 | 7/2004 | Wolinsky et al. |
| 6,782,810 | B2 | 8/2004 | Vilo |
| 6,783,499 | B2 | 8/2004 | Schwartz |
| 6,792,308 | B2 | 9/2004 | Corbucci |
| 6,792,311 | B2 | 9/2004 | Fox et al. |
| 6,805,667 | B2 | 10/2004 | Christopherson et al. |
| 6,809,507 | B2 | 10/2004 | Morgan et al. |
| 6,824,512 | B2 | 11/2004 | Warkentin et al. |
| 6,832,112 | B1 | 12/2004 | Bornzin |
| 6,840,956 | B1 | 1/2005 | Wolinsky et al. |
| 6,855,115 | B2 | 2/2005 | Fonseca et al. |
| 6,859,665 | B2 | 2/2005 | Ding et al. |
| 6,865,419 | B2 | 3/2005 | Mulligan et al. |
| 6,868,346 | B2 | 3/2005 | Larson et al. |
| 6,869,404 | B2 | 3/2005 | Schulhauser et al. |
| 6,871,088 | B2 | 3/2005 | Chinchoy |
| 6,885,889 | B2 | 4/2005 | Chinchoy |
| 6,889,086 | B2 | 5/2005 | Mass et al. |
| 6,895,265 | B2 | 5/2005 | Silver |
| 6,907,285 | B2 | 6/2005 | Denker et al. |
| 6,915,162 | B2 | 7/2005 | Noren et al. |
| 6,926,670 | B2 | 8/2005 | Rich et al. |
| 6,937,900 | B1 | 8/2005 | Pianca et al. |
| 6,949,075 | B2 | 9/2005 | Hatlestad et al. |
| 6,961,448 | B2 | 11/2005 | Nichols et al. |
| 6,970,742 | B2 | 11/2005 | Mann et al. |
| 6,978,182 | B2 | 12/2005 | Mazar et al. |
| 6,985,773 | B2 | 1/2006 | Von Arx et al. |
| 6,993,393 | B2 | 1/2006 | Von Arx et al. |
| 7,003,350 | B2 | 2/2006 | Denker et al. |
| 7,018,336 | B2 | 3/2006 | Enegren et al. |
| 7,024,248 | B2 | 4/2006 | Penner et al. |
| 7,033,322 | B2 | 4/2006 | Silver |
| 7,035,684 | B2 | 4/2006 | Lee |
| 7,047,065 | B2 | 5/2006 | Kalgren et al. |
| 7,060,030 | B2 | 6/2006 | Von Arx et al. |
| 7,061,381 | B2 | 6/2006 | Forcier et al. |
| 7,088,254 | B2 | 8/2006 | Liebenow |
| 7,127,290 | B2 | 10/2006 | Girouard et al. |
| 7,134,999 | B2 | 11/2006 | Brauker et al. |
| 7,136,703 | B1 | 11/2006 | Cappa et al. |
| 7,160,252 | B2 | 1/2007 | Cho et al. |
| 7,195,594 | B2 | 3/2007 | Eigler et al. |
| 7,200,439 | B2 | 4/2007 | Zdeblick et al. |
| 7,203,545 | B2 | 4/2007 | Schmitt et al. |
| 7,204,798 | B2 | 4/2007 | Zdeblick et al. |
| 7,209,790 | B2 | 4/2007 | Thompson et al. |
| 7,212,861 | B1 | 5/2007 | Park et al. |
| 7,214,189 | B2 | 5/2007 | Zdeblick |
| 7,236,821 | B2 | 6/2007 | Cates et al. |
| 7,248,923 | B2 | 7/2007 | Maile et al. |
| 7,273,457 | B2 | 9/2007 | Penner |
| 7,294,105 | B1 | 11/2007 | Islam |
| 7,335,161 | B2 | 2/2008 | Von Arx et al. |
| 7,399,313 | B2 | 7/2008 | Brown et al. |
| 7,425,200 | B2 | 9/2008 | Brockway et al. |
| 7,452,334 | B2 | 11/2008 | Gianchandani et al. |
| 7,481,771 | B2 | 1/2009 | Fonseca et al. |
| 2001/0051766 | A1 | 12/2001 | Gazdzinski |
| 2002/0023123 | A1 | 2/2002 | Madison |
| 2002/0042561 | A1 | 4/2002 | Schulman et al. |
| 2002/0045812 | A1 | 4/2002 | Ben-Haim et al. |
| 2002/0045836 | A1 | 4/2002 | Alkawwas |
| 2002/0120204 | A1 | 8/2002 | Pfeiffer et al. |
| 2002/0126036 | A1 | 9/2002 | Flaherty et al. |
| 2002/0147406 | A1 | 10/2002 | von Segesser |
| 2002/0151770 | A1 | 10/2002 | Noll, III et al. |
| 2002/0183628 | A1 | 12/2002 | Reich et al. |
| 2002/0188323 | A1 | 12/2002 | Penner et al. |
| 2003/0009204 | A1 | 1/2003 | Amundson et al. |
| 2003/0114897 | A1 | 6/2003 | Von Arx et al. |

| | | | |
|---|---|---|---|
| 2003/0136417 A1 | 7/2003 | Fonseca et al. | |
| 2003/0181794 A1 | 9/2003 | Rini et al. | |
| 2003/0191383 A1 | 10/2003 | Ben-Haim et al. | |
| 2003/0199779 A1 | 10/2003 | Muhlenberg et al. | |
| 2004/0032187 A1 | 2/2004 | Penner et al. | |
| 2004/0044393 A1 | 3/2004 | Yarden et al. | |
| 2004/0064133 A1 | 4/2004 | Miller et al. | |
| 2004/0077937 A1 | 4/2004 | Yarden | |
| 2004/0122484 A1 | 6/2004 | Hatlestad et al. | |
| 2004/0122486 A1 | 6/2004 | Stahmann et al. | |
| 2004/0152999 A1 | 8/2004 | Cohen et al. | |
| 2004/0158163 A1 | 8/2004 | Cohen et al. | |
| 2004/0167416 A1 | 8/2004 | Lee | |
| 2004/0172081 A1 | 9/2004 | Wang | |
| 2004/0204744 A1 | 10/2004 | Penner et al. | |
| 2005/0056539 A1 | 3/2005 | Morgan et al. | |
| 2005/0102002 A1 | 5/2005 | Salo et al. | |
| 2005/0124904 A1 | 6/2005 | Roteliuk | |
| 2005/0137490 A1 | 6/2005 | Scheiner et al. | |
| 2005/0149143 A1* | 7/2005 | Libbus et al. | 607/44 |
| 2005/0154321 A1 | 7/2005 | Wolinsky et al. | |
| 2005/0159639 A1 | 7/2005 | Skliar et al. | |
| 2005/0159789 A1 | 7/2005 | Brockway et al. | |
| 2005/0182330 A1 | 8/2005 | Brockway et al. | |
| 2005/0187482 A1 | 8/2005 | O'Brien et al. | |
| 2005/0192637 A1* | 9/2005 | Girouard et al. | 607/3 |
| 2005/0192844 A1 | 9/2005 | Esler et al. | |
| 2005/0197585 A1 | 9/2005 | Brockway et al. | |
| 2005/0215887 A1 | 9/2005 | Ben-Haim et al. | |
| 2005/0242479 A1 | 11/2005 | Petisce et al. | |
| 2005/0288727 A1 | 12/2005 | Penner | |
| 2006/0009818 A1 | 1/2006 | Von Arx et al. | |
| 2006/0031378 A1 | 2/2006 | Vallapureddy et al. | |
| 2006/0064133 A1 | 3/2006 | Von Arx et al. | |
| 2006/0064134 A1 | 3/2006 | Mazar et al. | |
| 2006/0064142 A1 | 3/2006 | Chavan et al. | |
| 2006/0064143 A1 | 3/2006 | Von Arx et al. | |
| 2006/0085039 A1 | 4/2006 | Hastings et al. | |
| 2006/0085041 A1 | 4/2006 | Hastings et al. | |
| 2006/0085042 A1 | 4/2006 | Hastings et al. | |
| 2006/0089694 A1 | 4/2006 | Zhang et al. | |
| 2006/0136004 A1 | 6/2006 | Cowan et al. | |
| 2006/0142651 A1 | 6/2006 | Brister et al. | |
| 2006/0235323 A1 | 10/2006 | Hatib et al. | |
| 2007/0043394 A1 | 2/2007 | Zhang et al. | |
| 2007/0049977 A1 | 3/2007 | Von Arx et al. | |
| 2007/0129765 A1 | 6/2007 | Gilkerson et al. | |
| 2007/0142727 A1 | 6/2007 | Zhang et al. | |
| 2007/0161914 A1 | 7/2007 | Zdeblick et al. | |
| 2008/0015421 A1 | 1/2008 | Penner | |
| 2008/0021333 A1 | 1/2008 | Huelskamp | |
| 2008/0021972 A1 | 1/2008 | Huelskamp et al. | |
| 2008/0046037 A1 | 2/2008 | Haubrich et al. | |
| 2008/0071178 A1 | 3/2008 | Greenland et al. | |
| 2008/0077440 A1 | 3/2008 | Doron | |

FOREIGN PATENT DOCUMENTS

| | | |
|---|---|---|
| EP | 0928598 | 7/1999 |
| EP | 1266606 | 12/2002 |
| EP | 1169085 | 8/2004 |
| WO | WO83/03345 | 10/1983 |
| WO | WO95/03086 | 2/1995 |
| WO | WO95/27531 | 10/1995 |
| WO | WO97/01986 | 1/1997 |
| WO | WO 97/18856 | 5/1997 |
| WO | WO97/32519 | 9/1997 |
| WO | WO97/33513 | 9/1997 |
| WO | WO97/47236 | 12/1997 |
| WO | WO98/26716 | 6/1998 |
| WO | WO98/29030 | 7/1998 |
| WO | WO99/17095 | 4/1999 |
| WO | WO99/26530 | 6/1999 |
| WO | WO99/34453 | 7/1999 |
| WO | WO99/47205 | 9/1999 |
| WO | WO99/55223 | 11/1999 |
| WO | WO99/55225 | 11/1999 |
| WO | WO99/59460 | 11/1999 |
| WO | WO99/66988 | 12/1999 |
| WO | WO00/16686 | 3/2000 |
| WO | WO00/58744 | 10/2000 |
| WO | WO01/28627 | 4/2001 |
| WO | WO01/56467 | 8/2001 |
| WO | WO01/74278 | 10/2001 |
| WO | WO02/03347 | 1/2002 |
| WO | WO02/32502 | 4/2002 |
| WO | WO03/002243 | 1/2003 |
| WO | WO03/096889 | 11/2003 |
| WO | WO2005/089638 | 9/2005 |
| WO | WO2005/118056 | 12/2005 |
| WO | WO2006/033812 | 3/2006 |
| WO | WO2006/034183 | 3/2006 |
| WO | WO2006/045073 | 4/2006 |
| WO | WO2006/045074 | 4/2006 |
| WO | WO2006/045075 | 4/2006 |
| WO | WO2006/069215 | 6/2006 |
| WO | WO2007/047287 | 4/2007 |
| WO | WO2007/070794 | 6/2007 |
| WO | WO2007/099533 | 9/2007 |
| WO | WO2008/011570 | 1/2008 |
| WO | WO2008/011592 | 1/2008 |
| WO | WO2008/011593 | 1/2008 |
| WO | WO2008/154145 | 12/2008 |

OTHER PUBLICATIONS

B. C. Penney et al., "Simplified electrode array for impedance cardiography," Medical & Biological Engineering & Computing, 1985, 23, p. 1-7.

B. Henderson et al., "Interaction of Photodynamic Therapy and Hyperthermia: Tumor Response and Cell Survival after Treatment of Mice in Vivo," Cancer Research, vol. 45, 6071 (Dec. 1985).

Bennett et al., "Subcutaneous pressure measurement as a surrogate for an external pressure reference for chronic implantable pressure monitoring," Journal of Cardial Failure, Churchill Livingstone, vol. 9, No. 5, p. S51, Oct. 1, 2003, abstract only.

Bonnefoy E, Ninet J, Robin J, Leroux F, Boissonat P, Brule P, Champsaur G., 1994, Bipolar intramyocardial electrogram from an implanted telemetric pacemaker for the diagnosis of cardiac allograft rejection, Pacing Clin Electrophysiol, 17(11 Pt 2):2052-6.

C. Hierold et al. (Germany, 1998) "Implantable Low Power Integrated Pressure Sensor System for Minimal Invasive Telemetric Patient Monitoring" IEEE, pp. 568-573.

Dipl.-Ing. Torsten Eggers et al. (Germany) "Implantable Telemetric Endosytem (ITES)" IMSAS Institut Fur Mikrosensoren-Aktuatoren Und-Systeme. 2 pp.

E R. Cosman et al. (Massachussetts, Apr. 1979) "A Telemetric Pressure Sensor for Ventricular Shunt Systems" Surgical Neurology vol. 11, No. 4, pp. 287-294.

G.W.H. Schurink et al. (1998) "Late Endoleak After Endovascular Therapy for Abdominal Aortic Aneurysm" Eur. J. Vasc. Endovasc. Surg. vol. 17, pp. 448-450.

Gerhausser A, Reichel T, Neukomm P A, Bolz A, Hugel J, Schaldach M, 1997, Diagnosis of rejection after kidney transplantation by impedance spectroscopy with an implantable measuring system, Biomed Tech (Berl), 42 Suppl. 160-1.

GH White et al. (1997) "Endoleak Following Endoluminal Repair of AAA: Management Options and Patient Outcomes", J. Endovasc Surg, pp. 1-45.

Graichen et al., "Patient Monitoring System for Load Measurement with Spinal Fixation Devices," Med. Eng. Phys. 18, (1996), pp. 167-174.

Haas et al., "Photodynamic Effects of Dyes on Bacteria," Published in Mutation Research, 1979, vol. 60, pp. 1-11.

Hashima et al., "Nonhomogenous Analysis of Epicardial Strain Distributions During Acute Myocardial Ischemia in the Dog," J Biomech 1993, Jan. 26: 19-35.

Hetzer R. et al., 1998, Daily non-invasive rejection monitoring improves long-term survival in pediatric heart transplantation, Ann. Thorac. Surg. (66):1343-1349.

J.A. Parrish, "Photobiologic Consideration on Photoradiation Therapy," pp. 91-108, Porphyrin Photosensitization, Plenum Press, (1983).

K.E. Uhrich et al., "Synthesis and characterization of degradable poly(anhydride-co-imides)", Macromolecules, 1995, 28, 2184-93.

Karl E. Richard et al. (Germany, Jan. 1999) "First clinical results with a telemetric shunt-integrated ICP-sensor" Neurological Research vol. 21, pp. 117-120.

Labrousse and Satre, "Photodynamic Killing of Dictyostelium Discoideum Amoebae Mediated by 4',5'-Diiodoflurescin Isothiocyanate Dextran. A strategy for the isolation of Thermoconditional Endocytosis Mutants," published in Photochemistry and Photobiology, 1993, vol. 67, No. 3, pp. 531-537.

Mackay et al., "Bio-medical Telemetry: Sensing and Transmitting Biological Information from Animals and Man," John Wiley & Sons, Inc. New York (1970) pp. 244-245.

Pfitzmann R, Muller J, Grauhan O. Cohnert T, Hetzer R, Z Kardiol, 1998, Measuring bioelectric myocardial impedance as a non invasive method for diagnosis of graft rejection after heart transplantation, 87(4):258-266.

Pirolo J S, Shuman T S, Brunt E M, Liptay M J, Cox J L, Ferguson T B Jr., J Thoracic Cardiovasc Surg, 1992, Noninvasive detection of cardiac allograft rejection by prospective telemetric monitoring, 103(5):969-79.

Prof. Dr. Johannes Zacheja et al. (Germany, Sep. 1996) "An Implantable Microsystem for Biomedical Applications" Micro System Technologies 96, pp. 717-722.

S.K. Gupta et al. (1999) "Use of a Piezoelectric Film Sensor for Monitoring Vascular Grafts", The American Journal of Surgery, vol. 160, pp. 182-186.

T. Chuter et al. (Sweden, Jan. 1997) "Aneurysm Pressure Following Endovascular Exclusion" Eur. J. Vasc. Endovasc. Surg. vol. 13, pp. 85-87.

T.A. Cochran et al. (1990) "Aortic Aneurysm Abdominal", Current Therapy in Adult Medicine, Fourth Edition.

Z. Tang et al. (May 1995) "Data Transmission from an Implantable Biotelemeter by Load-Shift Keying Using Circuit Configuration Modulator" IEEE Transactions on Biomedical Engineering. vol. 42, No. 5, pp. 524-528.

Bourgeois, Maurice J. et al., "Continuous Determination of Beat-to-Beat Stroke Volume from Aortic pressure Pulses in the Dog", Circulation Research, vol. 39, pp. 15-24 (1976).

Rozenman, Yoseph et al., "Wireless Acoustic Communication With a Miniature Pressure Sensor in the Pulmonary Artery for Disease Surveillance and Therapy of Patients With Congestive Heart Failure", Journal of the American College of Cardiology, 49:7, 2007, pp. 784-789.

Wesseling, KH et al., "Computation of Aortic Flow From Pressure in Humans Using a Nonlinear, Three-Element Model", Journal of Applied Physiology, vol. 74, Issue 5, pp. 2566-2573 (1993).

Fink, Mathias, "Time Reversal of Ultrasonic Fields—Part I: Basic Principles", IEEE Transactions on Ultrasonics, Ferroelectrics, and Frequency Control, vol. 39, No. 5, Sep. 1992, pp. 555-566.

International Search Report and Written Opinion issued in PCT/US2009/033436, mailed May 27, 2009, 12 pages.

Wu, Francois et al., "Time Reversal of Ultrasonic Fields—Part II: Experimental Results", IEEE Transactions on Ultrasonics, Ferroelectrics, and Frequency Control, vol. 39, No. 5, Sep. 1992, pp. 567-578.

Strickberger, S. Adam et al., "Extracardiac Ablation of the Canine Atrioventricular Junction by Use of High-Intensity Focused Ultrasound", Circulation, Jul. 13, 1999; downloaded from circ.ahajournals.org at ACS/GUIDANT on Jan. 4, 2008, pp. 203-208.

Cohen, T.J. et al., "A Hemodynamically Responsive Antitachycardia System. Development and Basis for Design in Humans", Circulation 1990, vol. 82, No. 2, pp. 394-406, XP002560584.

Blacher, Jacques et al., "Aortic Pulse Wave Velocity as a Member of Cardiovascular Risk in Hypertensive Patients", Hypertension May 1999;33;1111-1117.

Farzaneh-Far, Ramin et al., Usefulness of Noninvasive Estimate of Pulmonary Vascular Resistance to predict Mortality, Heart Failure, and Adverse Cardiovascular Events in Patients With Stable Coronary Artery Disease (from the Heart and Soul Study), The American Journal of Cardiology, vol. 101, Issue 6, Mar. 15, 2008, pp. 762-766.

El Gamal, M.I.H. et al., "Chronic Ventricular Pacing With Ventriculo-Atrial Conduction Versus Atrial Pacing in Three Patients With Symptomatic Sinus Bradycardia", PACE, vol. 4, Jan.-Feb. 1981, pp. 100-106.

Fujiki, Akira et al., "Pacemaker Syndrome Evaluated by Cardiopulmonary Exercise Testing", PACE, vol. 13, Oct. 1990, pp. 1236-1241.

* cited by examiner

USING IMPLANTED SENSORS FOR FEEDBACK CONTROL OF IMPLANTED MEDICAL DEVICES

TECHNICAL FIELD

The present invention relates to methods and devices for administering cardiac therapy using implantable medical devices. More specifically, the invention relates to methods and devices for utilizing pulmonary arterial pressure to control the operation of a cardiac therapy device.

BACKGROUND

As one skilled in the art will appreciate, blood pressure in the left ventricle, and in particular left ventricular end diastolic pressure, is a useful physiologic parameter for evaluating and monitoring cardiac performance. This left ventricular pressure can serve useful in predicting the onset of pulmonary edema in congestive heart failure patients, monitoring and treating hypertension, optimizing the operation of cardiac rhythm management devices, and in rhythm discrimination. Unfortunately, the elevated fluid pressures in the left ventricle increase the likelihood of hemorrhage during or following placement of monitoring equipment such as pressure sensors within the left ventricle. Furthermore, because blood flows directly from the left ventricle to other parts of the body, including the brain, the risk of stroke or vessel blockage from thrombi formed in the left ventricle is significant. While pressure measurements within the right ventricle are more easily obtained, and at lower risk than the left ventricle, they are of less use in evaluating cardiac performance.

There is thus a need for a system for obtaining physiologic data relatable to left ventricular end diastolic pressure, from a location less susceptible to trauma than the left ventricle, to control the operation of a remotely located implantable medical device.

SUMMARY

In one embodiment, the present invention is a system for administering a therapeutic treatment to the heart. The system includes a pressure sensor adapted for positioning in the pulmonary artery and collecting data representative of at least one of systolic pressure, diastolic pressure, pulse pressure, heart rate or pre-ejection period based on pressure in the pulmonary artery. The system further includes an implantable medical device located remotely from the sensor and a control module operatively coupled to the implantable medical device and communication means for communicating pressure data from the pressure sensor to the control module. The control module is adapted for comparing the at least one of systolic pressure, diastolic pressure, pulse pressure, heart rate or pre-ejection period to a pre-programmed value, adjusting an operating parameter of the implantable medical device based on the relationship of the at least one of systolic pressure, diastolic pressure, pulse pressure, heart rate or pre-ejection period to the pre-programmed value, and repeating this process until the relationship is such that no adjustment is necessary.

In another embodiment, the present invention is a method of administering a therapeutic treatment to the heart. Pulmonary arterial pressure is sensed from within the pulmonary artery with an implanted sensor. Data representative of the sensed pulmonary arterial pressure is communicated from the sensor to an implanted medical device. A pre-ejection period is calculated from the data. It is determined if the pre-ejection period is changing in relation to previously calculated pre-ejection periods. If the pre-ejection period is changing, the heart rate is adjusted until subsequently measured pre-ejection periods are within an appropriate range.

According to another embodiment, the present invention is a method of administering a therapeutic treatment to the heart. Pulmonary arterial pressure is sensed from within the pulmonary artery with an implanted sensor. Data representative of the sensed pulmonary arterial pressure is communicated from the sensor to an implanted medical device. The data is compared to a pre-programmed value relating to pulmonary arterial pressure. Increases in the heart's pacing rate are limited to maintain the pulmonary arterial pressure below the pre-programmed value.

In yet another embodiment, the present invention is a method of administering a therapeutic treatment to the heart. Pulmonary arterial pressure is sensed from within the pulmonary artery with an implanted sensor. Data representative of the sensed pulmonary arterial pressure is communicated from the sensor to an implanted medical device. Heart rate and pulse pressure are calculated. It is determined if, based on heart rate and pulse pressure, a ventricular arrhythmia is occurring, and (2) if so, whether the ventricular arrhythmia is potentially lethal. If a ventricular arrhythmia is present and is considered lethal, a defibrillation shock is administered. If a ventricular arrhythmia is present but is not considered lethal, an anti-tachy pacing protocol is administered.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Figure 1:
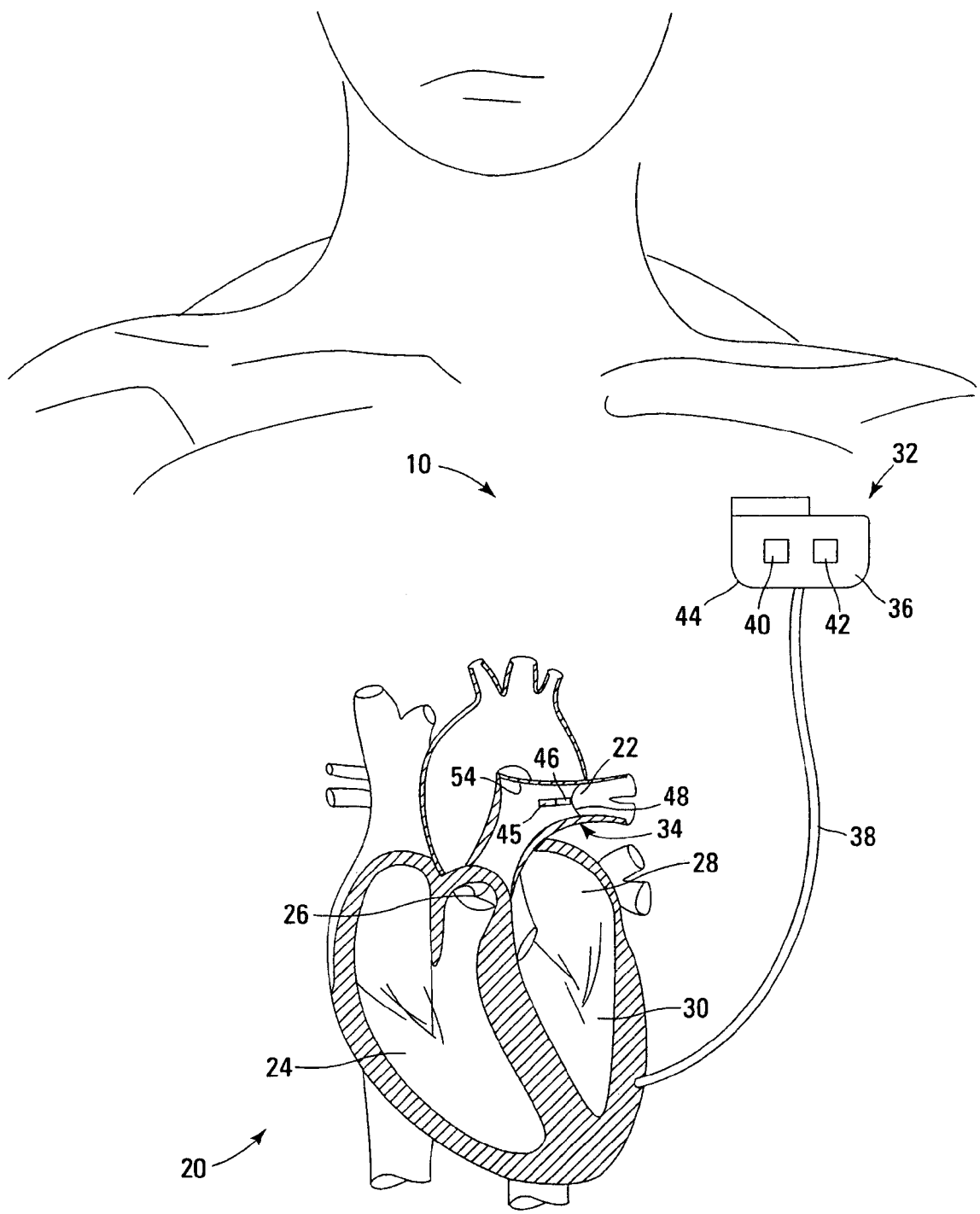
FIG. 1 shows a schematic view of a system for administering a therapeutic treatment to the heart, in accordance with an embodiment of the present invention, in relation to a heart.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The present invention relates generally to a method and system for administering a therapeutic treatment to the heart, and more specifically to a method and system in which blood pressure measurements are obtained and incorporated into the closed-loop control of a remotely located implantable medical device. As one skilled in the art will appreciate, blood pressure can be obtained from a number of different locations, such as the pulmonary artery, the aorta, anywhere in the arterio-venous system, or many locations distal from the heart. Different symptoms and/or diseases can be determined by measuring pressure at different locations. Furthermore, a measurement of pressure at one location can be indicative of or relatable to a physiologic parameter at a second location. Thus, the present invention is not limited to detecting pressure at any particular location. However, for ease of discussion, the methods and systems will be described with reference to placing sensors in the pulmonary artery.

FIG. 1 shows a system 10 for administering a therapeutic treatment in relation to a human heart 20 in accordance with an embodiment of the present invention. As shown in FIG. 1, the heart 20 includes a pulmonary artery 22, which carries deoxygenated blood from a right ventricle 24 to the lungs (not shown). Fluid flow into the pulmonary artery 22 is regulated by the opening and closing of the passive pulmonary valve 26. When the right ventricle 24 contracts during systole, the pulmonary valve 26 opens and blood flows into the pulmonary artery 22. When the right ventricle 24 relaxes during diastole, the pulmonary valve 26 closes to prevent backwash of blood from the pulmonary artery 22 into the right ventricle 24. The increase or decrease of fluid pressure within the pulmonary artery 22 corresponds to the opening and closing of the pulmonary valve 26, which directly follows contractions of the right ventricle 24. Thus, among other things, the rise and fall of blood pressure within the pulmonary artery 22 provides an accurate measure of right side pacing of the heart 20. Oxygenated blood flows from the lungs into a left atrium 28 and into a left ventricle 30 of the heart 20. The left ventricle 30 in turn pumps the oxygenated blood out the aorta to the rest of the body.

The system 10 includes an implantable medical device (IMD) 32 in communication with a pressure sensor unit 34 positioned in the pulmonary artery 22. Exemplary IMDs 32 for use in conjunction with the present invention include implantable cardiac devices, such as pacemakers, defibrillators, ventricular assist devices (VADs), drug pumps, cardiac resynchronization therapy (CRT) devices, and stand-alone diagnostic devices for enhancing the utility of tachycardia and bradycardia devices relative to disorders such as vasovagal syncope. Other exemplary IMDs 32 are devices used for post-implant monitoring of the functionality of passive devices like septal plugs and artificial valves.

In the embodiment shown generally in FIG. 1, the IMD 32 is a cardiac rhythm management device including a pulse generator 36 implanted subdermally in the upper chest or abdomen and an electrical lead 38 extending from the pulse generator 36 into the heart 20 for sensing or pacing the heart 20. The IMD 32 further includes receiving communication means 40 for receiving data from the pressure sensor 34 and a control module 42 for interpreting the data from the sensor unit 34 and controlling at least part of the IMD 32 operation. The communication means 40 and control module 42 may be located in a housing 44 along with the pulse generator 36. The control module 42 is operatively coupled to the IMD 32 and controls and adjusts the operating parameters of the IMD 32.

As is shown in FIG. 1, the pressure sensor unit 34 is positioned in the pulmonary artery 22. The pressure sensor unit 34 includes a sensor or transducer 45 for obtaining pressure data and sending communication means 46 for communicating data from the sensor 34 to the IMD 32.

Exemplary sensors and sensor configurations are described in more detail in the following four co-pending patent applications: U.S. patent application. Ser. No. 10/943,626 entitled "SYSTEMS AND METHODS FOR DERIVING RELATIVE PHYSIOLOGIC PARAMETERS," filed Sep. 17, 2004; U.S. patent. application Ser. No. 10/943,269 entitled "SYSTEMS AND METHODS FOR DERIVING RELATIVE PHYSIOLOGIC PARAMETERS USING AN EXTERNAL COMPUTING DEVICE," filed Sep. 17, 2004; U.S. patent application Ser. No. 10/943,627 entitled "SYSTEMS AND METHODS FOR DERIVING RELATIVE PHYSIOLOGIC PARAMETERS USING A BACKEND COMPUTING SYSTEM," filed Sep. 17, 2004; and U.S. patent application Ser. No. 10/943,271 entitled "SYSTEMS AND METHODS FOR DERIVING RELATIVE PHYSIOLOGIC PARAMETERS USING AN IMPLANTED SENSOR DEVICE," filed Sep. 17, 2004. All of the above-identified patent applications are hereby incorporated by reference.

Figure 2:
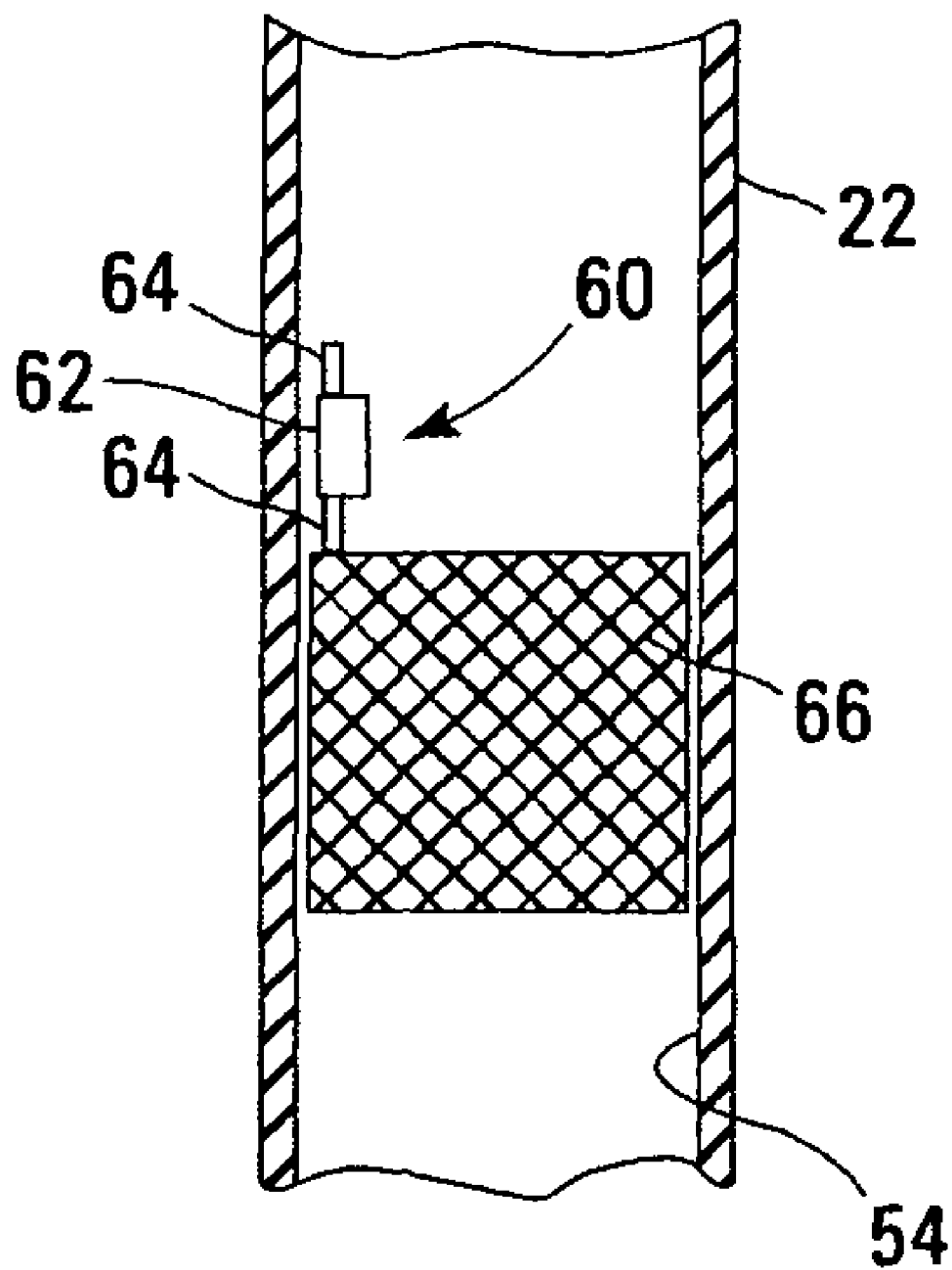
FIG. 2 shows a cross-sectional view of a sensor device being held in place in the pulmonary artery according to one embodiment of the present invention.

The sensor unit 34 further includes an anchoring system 48 for anchoring the pressure sensor 34 in the pulmonary artery 22. FIG. 2 shows a portion of the sensor unit in accordance with one embodiment of the present invention. The sensor 62 includes one or more fins or extensions 64 that can facilitate the anchoring of sensor 62 in the pulmonary artery 22. The sensor unit can be positioned within the pulmonary artery 22 and initially anchored or held in place using an expandable stent-like device 66. The stent-like device 66 can be any suitable stent device or other anchoring device currently known or hereinafter developed.

Figure 3:
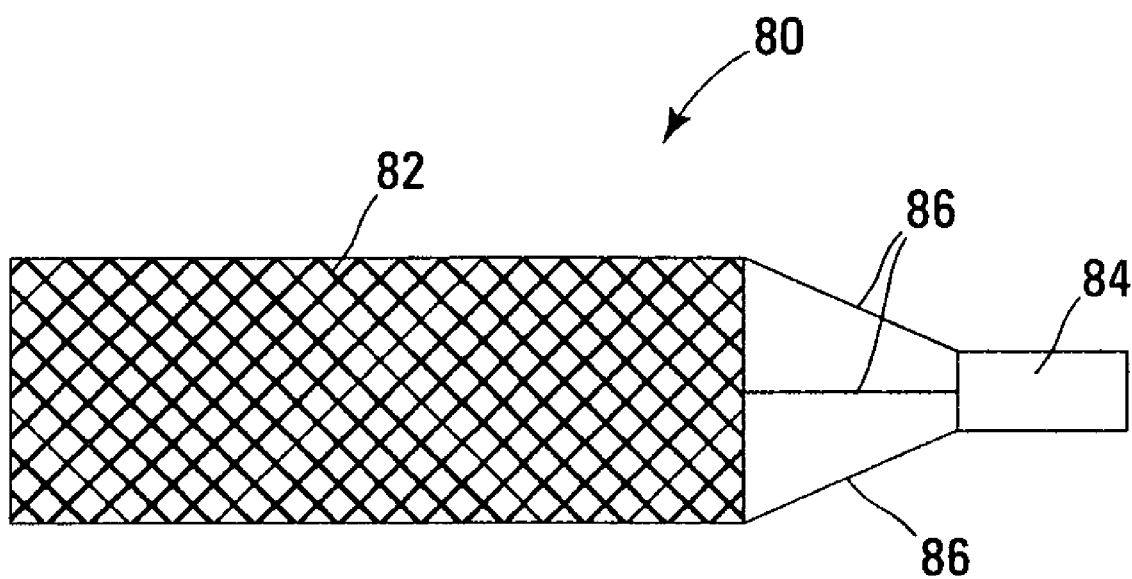
FIG. 3 shows another embodiment of an exemplary sensor anchoring device for use with the system of FIG. 1.

FIG. 3 shows a portion of a sensor unit according to another embodiment of the present invention. As shown in FIG. 3, the sensor unit 80 includes an anchoring device 82, a sensor 84, and one or more connection structures 86 for connecting the sensor 84 to the anchoring device 82. In this particular embodiment, the connection structures 86 are configured to secure the sensor 84 so that the sensor 84 will reside near the middle of the pulmonary artery 22, as opposed to the anchoring structure discussed above that position the sensor near the vessel wall 54. By placing the sensor 84 near the middle of the pulmonary artery 22, the sensor 84 will reside in the predominant blood flow that occurs in the middle of the pulmonary artery 22, avoiding edge effects, such as slower blood flow, dead zones, and perhaps clotting issues.

In one embodiment, the sensor unit 60, including the sensor 62 and the extensions 64, is formed from a bio-compatible material, such as stainless steel, titanium, Nitinol, or some other bio-compatible material. In yet other embodiments, the sensor unit can be coated with Dacron®, nylon, polyurethane or other material that promotes the formation of a layer of endothelial tissue over the device. In still other embodiments, the sensor unit 60 can be coated with one or more drugs to reduce inflammation and/or induce endothelialization. Such drugs are currently known in the art.

The sensor unit can be positioned and secured in the pulmonary artery 22 using techniques similar to a Swan-Ganz technique, or other similar catheterization techniques, which is further described in co-pending U.S. patent application Ser. No. 10/970,265, entitled "Delivery System and Method for Pulmonary Artery Leads," filed Oct. 21, 2004, which is hereby incorporated by reference.

As shown in FIG. 1, the sending communication means 46 of the pressure sensor 34 and the receiving communication means 40 of the IMD 32 may be wireless, in which case the IMD 32 and the pressure sensor 34 are not physically connected. Suitable sending communication means 46 and receiving communication means 40 include acoustic, ultrasonic and radio frequency wireless communication modules in communication with and operatively coupled to the pressure sensor 45 and control module 42, respectively. Such communication modules can further include shielding and antennas for facilitating the transfer of data and reducing background noise and interference.

Figure 4:
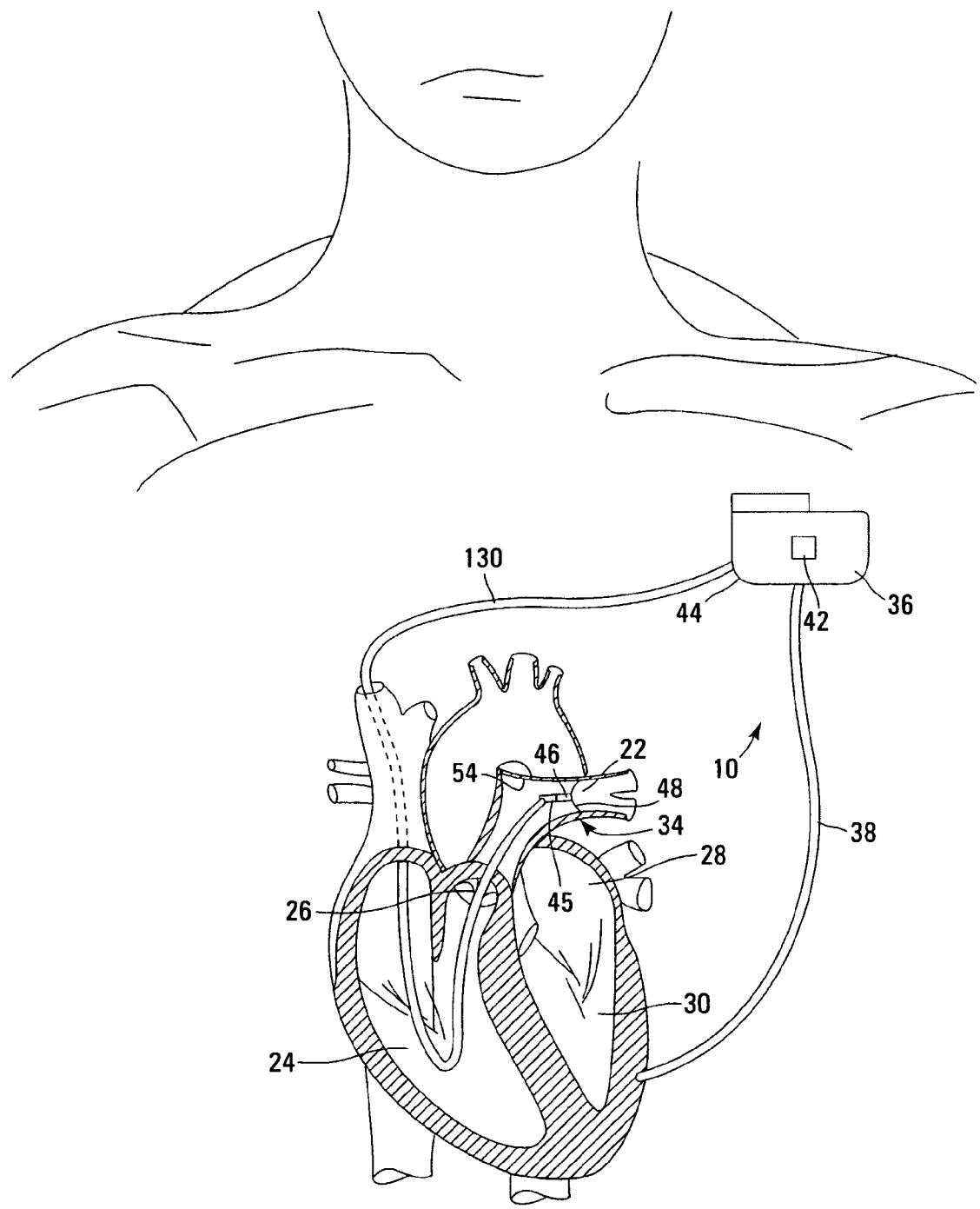
FIG. 4 shows a system for administering a therapeutic treatment to the heart in accordance with another embodiment of the present invention in relation to a heart.

FIG. 4 shows another embodiment, however, in which the sending communication means 46 and receiving communication means 40 are provided via a physical connection between the pressure sensor 45 and the IMD 32. In this embodiment, the sending communication means 46 and receiving communication means 40 are an electrical lead 130 extending from the pressure sensor 34 in the pulmonary artery 22, through the pulmonic valve 26, to the IMD 32. In other embodiments, the sending communication means 46 and the receiving communication means 40 are provided by a fiber optic connector.

The pulmonary arterial pressure sensor unit 34 is used to gather data concerning the amplitude, timing and/or morphology of blood pressure within the pulmonary artery 22. The sensor unit 34 may be used to monitor sudden changes in pressure or other critical events or to gather data over longer periods of time to determine cardiac performance trends. The sensor unit 34 may be programmed to continuously monitor pressure within the pulmonary artery 22, to sample pressure within the pulmonary artery 22 periodically, or to commence monitoring or sampling when a secondary event transpires. For example, the sensor 45 could be awakened or activated based on sensed heart rate or indications from other sensor(s). Alternately, the pulmonary arterial sensor 45 may be externally controlled, based on other sensor information or time, to reduce power consumption. In one embodiment, a measure of atmospheric pressure is provided to the sensor unit 34 to allow it to correct for atmospheric pressure in the generation of an accurate pulmonary arterial pressure reading.

Information about physiologic parameters such as blood pressure within the pulmonary artery 22 has intrinsic value in evaluating the mechanical operation and other characteristics of the cardio-pulmonary system. However, information about physiologic parameters within the pulmonary artery 22 can also be used to obtain information about secondary physiologic parameters. For example, as is known in the art, pressures measured in the pulmonary artery 22 can be reflective of end diastolic pressures on the left side of the heart 20 and within the left ventricle 30. Both pulmonary arterial end-diastolic pressure and mean pulmonary arterial pressure can be correlated with left ventricular end-diastolic pressure.

The correlated secondary physiologic parameter data, in this embodiment left ventricular end diastolic pressure data, may then be used to evaluate and monitor cardiac performance for use in controlling at least part of the operation of the IMD 32. Pressure data from the sensor unit 34 may be compared alone or in conjunction with other inputs the IMD 32 may have collected or been programmed with to a pre-programmed value or range. The relationship between the pressure data and any other inputs to the pre-programmed value or range may be used by the control module 42 to adjust the operating parameters of the IMD 32. The system 10 can continue to adjust the operating parameters of the IMD 32 as the relationship changes following the administration of a therapeutic treatment (i.e., the change in the operating parameters of the IMD 32) until the relationship is acceptable or until the relationship is such that further therapeutic treatment is unnecessary or prohibited, or a satisfactory outcome is reached. In this manner, the system 10 provides relatively straightforward closed-loop applications to control IMD 32 parameters and operation, and more specifically provides a closed-loop system for administering a therapeutic treatment to the heart 20 via the IMD 32.

The following examples describe various applications for administering a therapeutic treatment via system 10.

Figure 5:
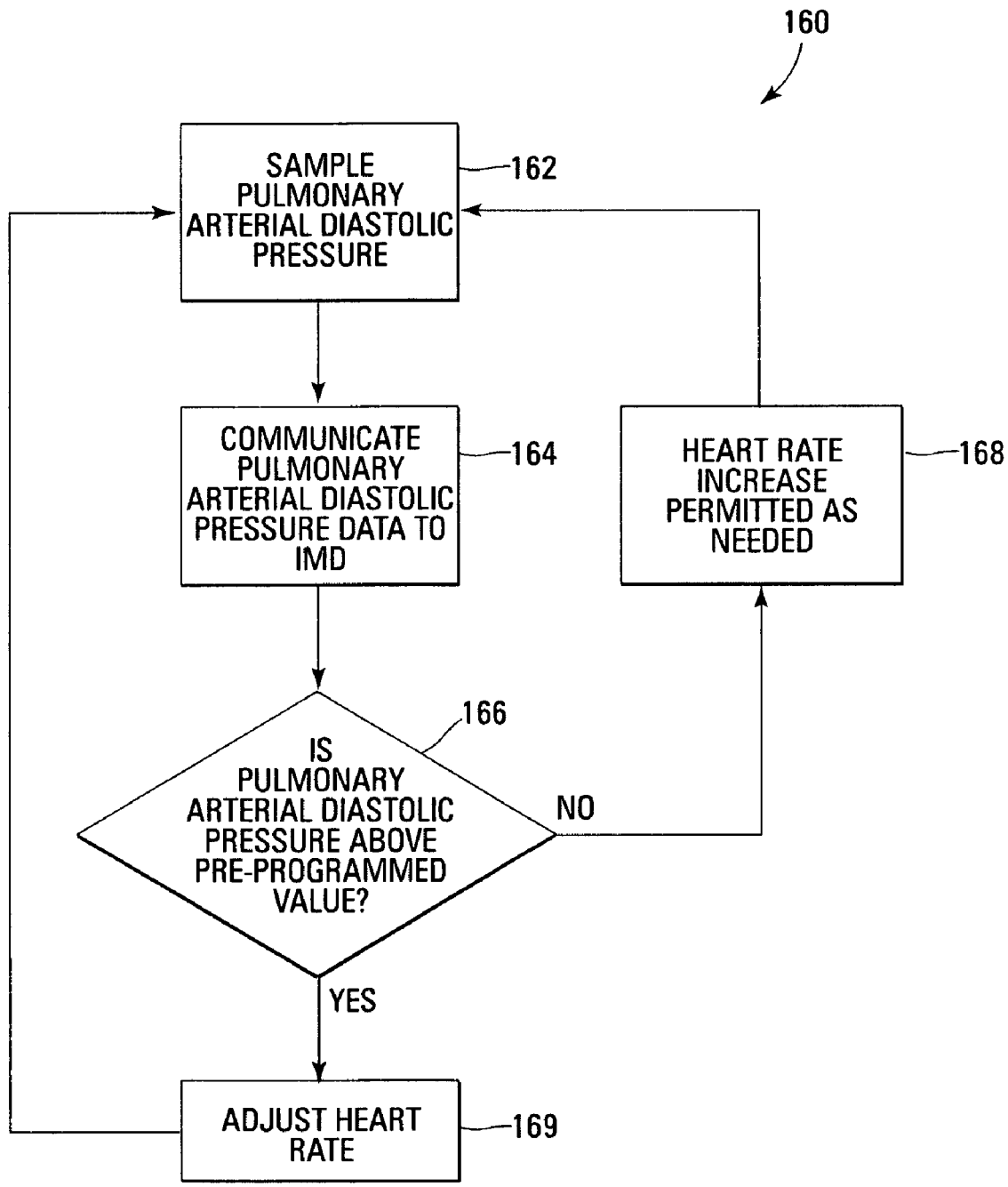
FIG. 5 is a flowchart illustrating a method of administering a therapeutic treatment to the heart in accordance with an embodiment of the present invention.

FIG. 5 is a flowchart illustrating a method 160 of administering a therapeutic treatment to the heart 20 in accordance with another embodiment of the present invention. In general, sick or diseased hearts do not beat as rapidly as healthy hearts. As a result, there must be more time between heartbeats for the pressure to decrease to a normal range of diastolic pressure (approximately 6-13 mmHg) in the pulmonary artery 22. An increase in heart rate will thus increase the pulmonary arterial diastolic pressure (PADP) in these patients into a range (approximately greater than 15-20 mmHg) where the patient would suffer dyspnea (abnormal or uncomfortable breathing). Simply reducing the rate will alleviate some of these symptoms, although, obviously, the patient will still have reduced exercise capacity, since reducing the maximum heart rate will reduce the maximum cardiac output attainable.

In the present method, the PADP is monitored (block 162) and data is communicated to the control module 42 in the IMD 32 (block 164). The control module 42 is adapted to control and adjust the pacing rate of IMD 32 based upon the relationship between the diastolic pressure and a pre-programmed value based upon normal or desired diastolic pressure. The pre-programmed value may be set by the physician or may be determined by the control module 42 based upon historic diastolic pressure measurements. In one embodiment, the control module 42 compares the PADP to the pre-programmed value and limits increases in the pacing rate of a cardiac rhythm management device (i.e., IMD 32) that would increase the pulmonary arterial diastolic pressure above the pre-programmed value (blocks 168 and 169). This application provides a symptom (i.e., increasing pulmonary arterial diastolic pressure) limited upper rate of the operation of the IMD 32 and can reduce exercise-induced dyspnea. Since other factors such as blood volume and posture can affect the PADP, the sensor based approach to rate control as just described will be more effective than simply programming a lower value for the upper rate limit (e.g., 100 beats/minute). This process may be repeated continuously or as needed to achieve a satisfactory outcome or relationship, i.e., to prevent exercise-induced dyspnea, or when the relationship between the diastolic pressure and the pre-programmed value is such that no further adjustment in IMD 32 operating parameters is desired.

Figure 6:
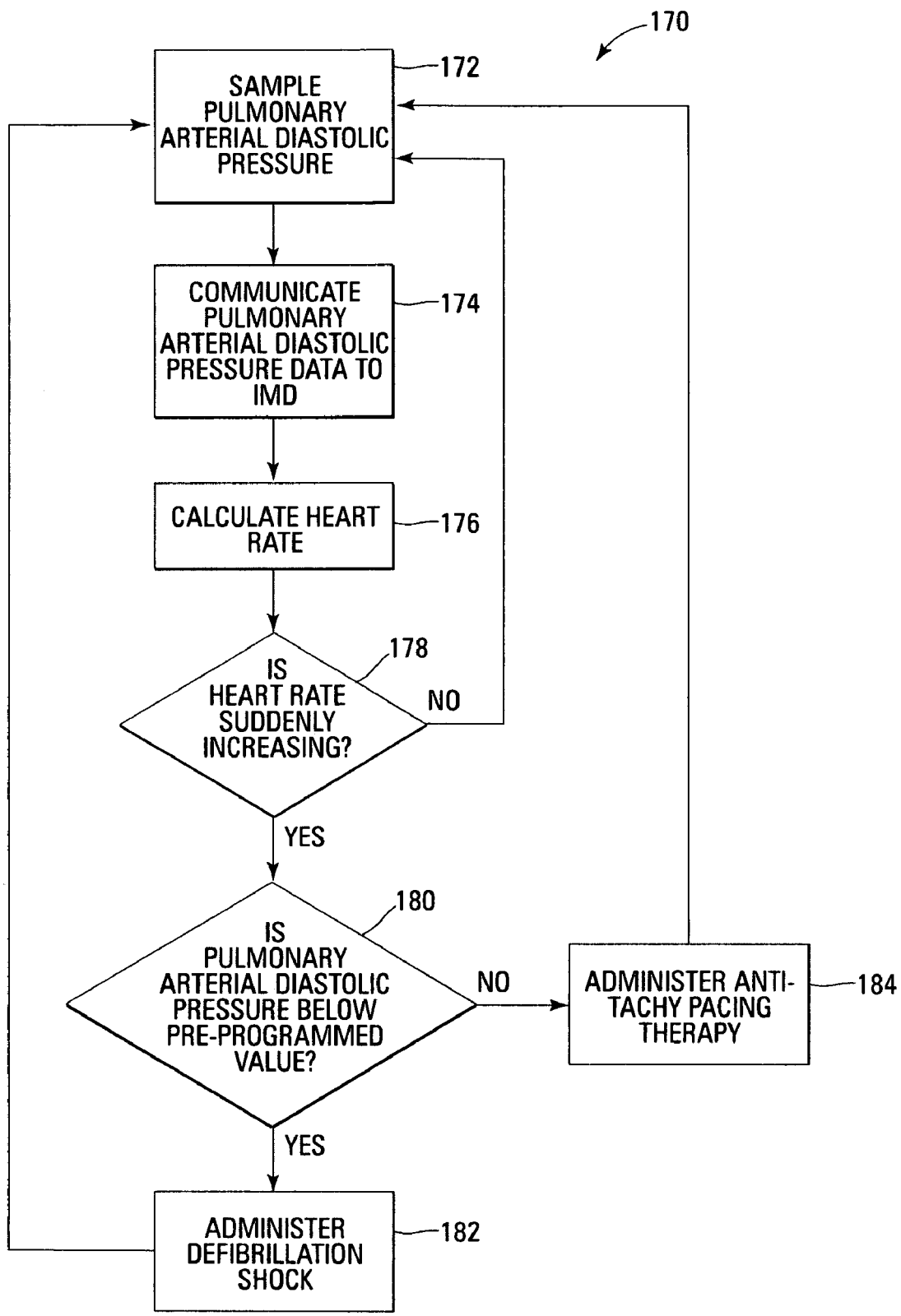
FIG. 6 is a flowchart illustrating a method of administering a therapeutic treatment to the heart in accordance with another embodiment of the present invention.

FIG. 6 is a flowchart illustrating a method 170 of administering a therapeutic treatment to the heart 20 according to yet another embodiment of the present invention. In the present embodiment, pulmonary arterial pulse pressure is monitored to identify potentially lethal ventricular arrhythmias, for example, ventricular tachycardias.

Ventricular tachycardias are sensed by implantable medical devices such as defibrillators in one of two ways: (1) by looking for a sustained heart rate that exceeds a pre-programmed value (e.g., 220 beats/minute) or (2) by looking for a sustained heart rate that exceeds a lower pre-programmed value (e.g., 180 beats/minute) but reaches this heart rate very quickly (e.g., a rate increase of 60 beats/minute in less than five seconds).

In addition to these criteria, if the pre-ejection period doesn't shorten significantly (e.g., greater than ten percent shortening) or if the systolic pulmonary arterial pressure simultaneously drops (e.g., greater than ten percent decrease), then the device could be relatively certain that the patient is experiencing a ventricular arrhythmia. If the decrease in systolic pulmonary arterial pressure were even greater (e.g., greater than fifty percent), this would indicate that the patient is unconscious and in serious danger and should receive a shock immediately to correct the arrhythmia. However, the shock could be delayed and the device could go through a series of anti-tachy pacing protocols if the systolic pulmonary arterial pressure remained above the threshold value.

Thus, pressure data from the pressure sensor unit 34 is gathered (block 172) and communicated to the control module 42 in the IMD 32 (block 174). The control module 42 is adapted to calculate the heart rate based upon changes in pulmonary arterial pressure over time (block 176) or from the intracardiac electrogram sampled from lead 38. Based upon the relationship between the calculated heart rate, diastolic pressure and a pre-programmed value or range, the control module 42 is further adapted to adjust and control the operating parameters of the IMD 32. In one embodiment, if along with a sudden increase in heart rate (block 178), the measured systolic pressure or pulse pressure drops by a pre-programmed percentage or absolute value (block 180), the ventricular arrhythmia is considered to be potentially lethal and the IMD 32 administers a defibrillation shock as soon as possible (block 182). However,. if the arrhythmia is not considered immediately lethal, an anti-tachy pacing protocol may be implemented via the IMD 32 to convert the patient less traumatically (block 184). This will potentially reduce the incidence of "unnecessary" shock treatment. Thus, based on the relationship between the PADP, heart rate and pulmonary arterial systolic or pulse pressure, which may be based on historic measurements, the control module 42 instructs the IMD 32 as to the appropriate course of action to adjust the IMD 32 operating parameters. This process may be repeated or looped until a satisfactory outcome or relationship between the sensed PADP, heart rate, pulse pressure or systolic pressure is achieved or maintained, or until the relationship between the diastolic pressure and the pre-programmed value is such that no further adjustment in IMD 32 operating parameters is desired.

Figure 7:
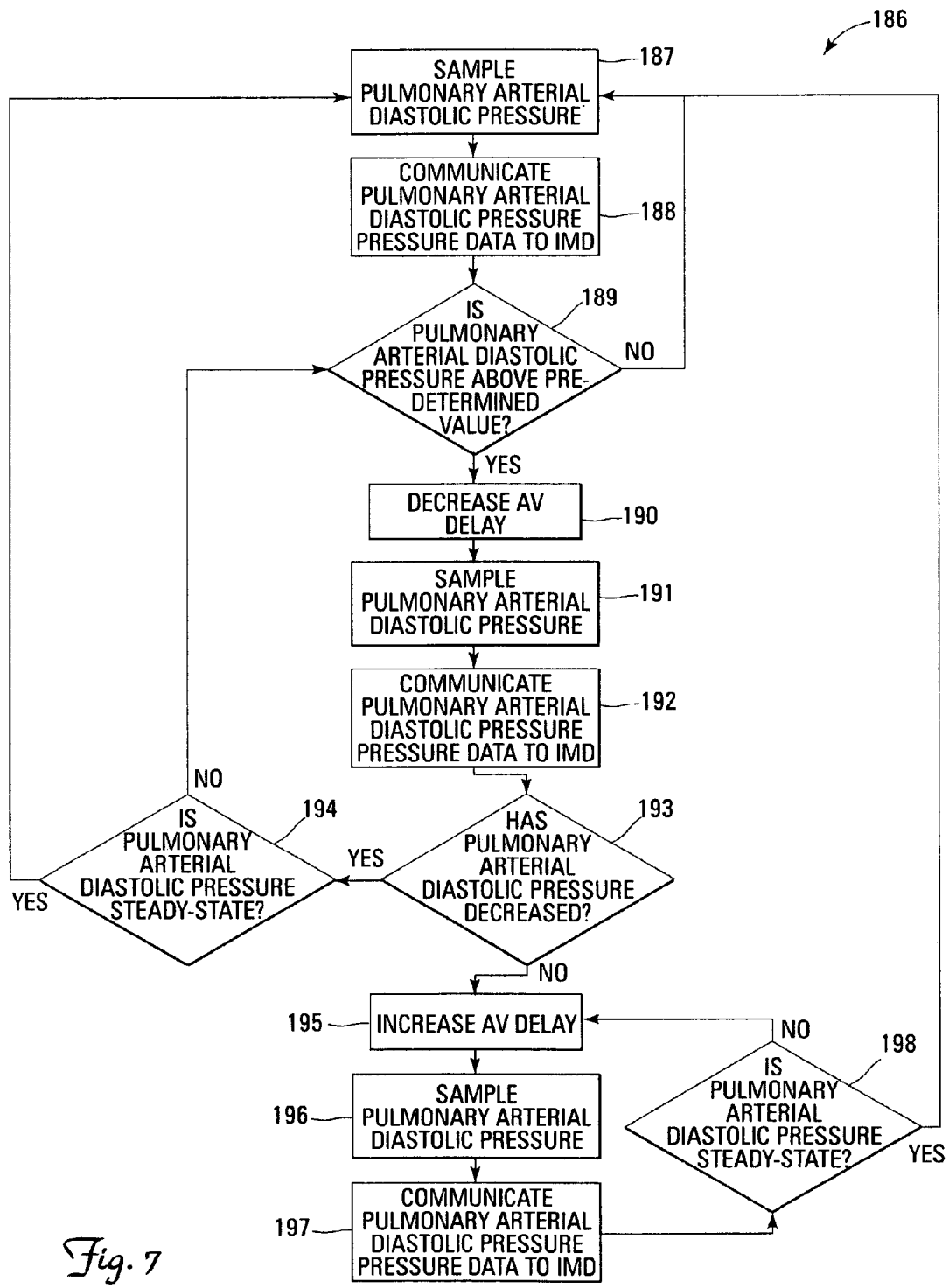
FIG. 7 is a flowchart illustrating a method of administering a therapeutic treatment to the heart in accordance with another embodiment of the present invention.

FIG. 7 is a flowchart illustrating a method 186 of administering a therapeutic treatment to the heart 20 in which atrial ventricular ("AV") delay is optimized for cardiac resynchronization therapy. PADP is monitored periodically by the pressure sensor 34 (block 187) and pressure date is communicated to the control module 42 in the IMD 32 (block 188). The relationship between the sensed PADP and a pre-programmed value relating to optimal or normal PADP, which may be based on historic measurements, is employed by the control module 42 to control the operating parameters of the IMD 32. In one embodiment, if the PADP is above a pre-programmed value relating to a normal or upper limit (usually 15-20 mm Hg) (block 189), the IMD 32 adjusts the AV delay until the diastolic pressure in the pulmonary artery 22 is reduced to an appropriate value. In one embodiment, the AV delay is first decreased (block 190). The PADP is sampled (block 191) and communicated to the IMD 32 (block 192). If the PADP has also decreased (block 193), the process is repeated in increments until a minimum steady—state PADP is reached (block 194). On the other hand, if decreasing the AV delay is accompanied by an increase in the PADP, then the AV delay is increased (block 195). The PADP is sampled (block 196), communicated to the IMD 32 (block 197) and repeated in increments until a minimum PADP is reached (198). This process may be repeated or looped until a satisfactory outcome or relationship between the sensed PADP and the pre-programmed value is achieved or maintained, or until the relationship between the diastolic pressure and the pre-programmed value is such that no further change in IMD 32 operating parameters is desired.

Figure 8:
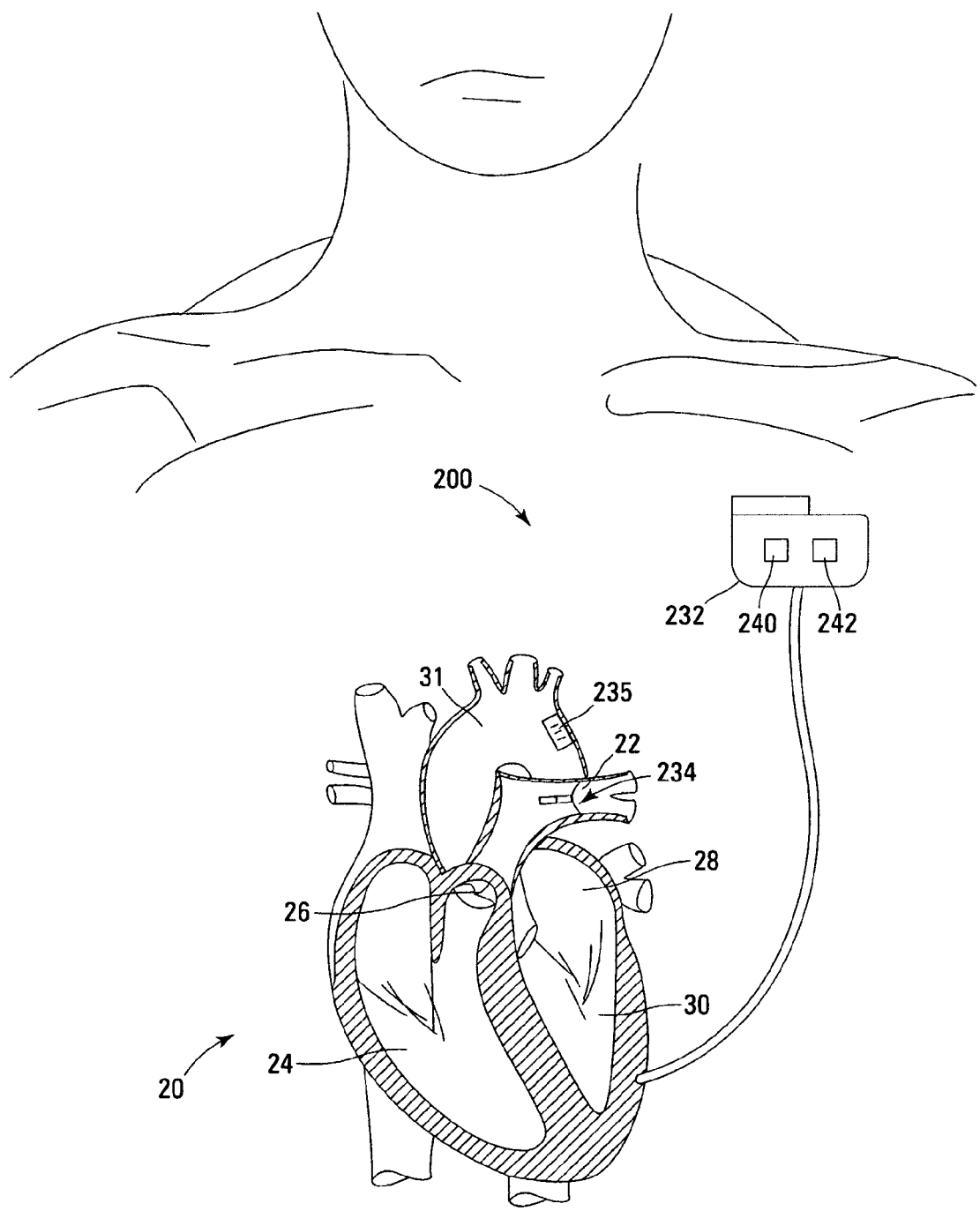
FIG. 8 shows a system for administering a therapeutic treatment to the heart in accordance with another embodiment of the present invention in relation to a heart.

In another embodiment of the present invention, the system includes a secondary sensor located remotely from the pulmonary arterial sensor. FIG. 8 shows a system 200 including an implantable medical device 232 in communication with a remotely located pressure sensor 234 positioned in the pulmonary artery 22 and a secondary sensor 235 located remotely from the pulmonary arterial sensor 234. The secondary sensor 235 is adapted for measuring a physiologic parameter, for example, blood pressure, at the second location. The secondary sensor 235 is also in communication with a control module 242 of the IMD 232. Information about the physiologic parameter received from the secondary sensor 235 may be used by the control module 242 in conjunction with information received from the pulmonary sensor 234 to control operation of the IMD 232. As is shown in FIG. 9, in one embodiment the secondary sensor 235 is a pressure sensor located in the aorta 31.

Figure 9:
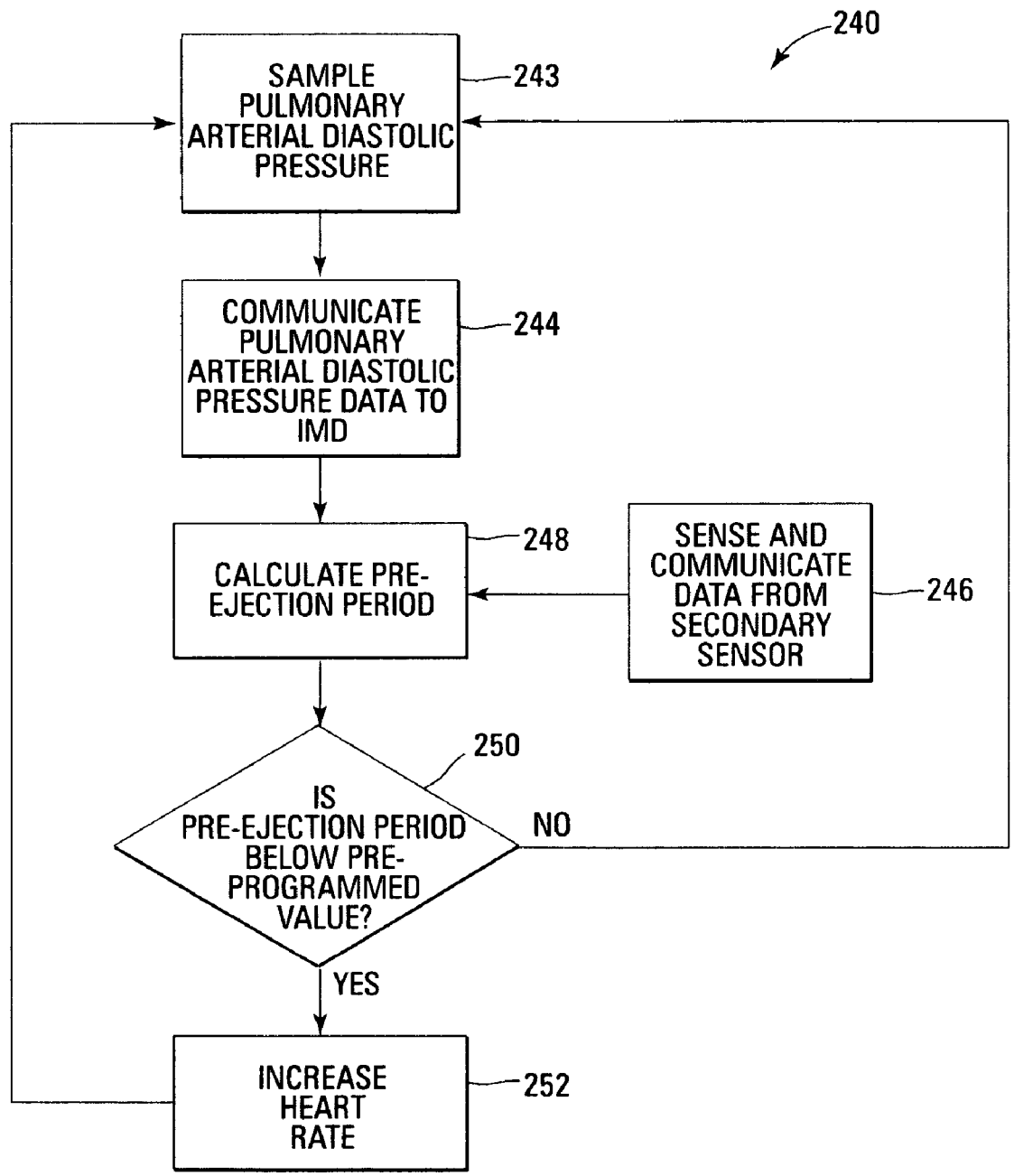
FIG. 9 is a flowchart illustrating a method of administering a therapeutic treatment to the heart in accordance with another embodiment of the present invention.

FIG. 9 is a flowchart illustrating a method 240 of administering a therapeutic treatment to the heart 20 in accordance with an embodiment of the present invention. The pressure sensor unit 34 detects the pressure within the pulmonary artery (block 243) and communicates pressure data to the control module 42 in the IMD 32 (block 244). The IMD 32 is also in communication with a secondary sensor (block 246). The secondary sensor may be, for example, an electrical lead positioned within a ventricle and adapted for sensing electrical activity within the ventricle. The control module 42 is adapted to determine the pre-ejection period based upon the pressure data communicated from the sensor unit 34 and the electrical data communicated from the lead (block 248).

It is known that changes in pre-ejection period, measured as the time between ventricular electrical sensing or pacing to the beginning of the increase in pulmonary arterial pressure (corresponding to the beginning of right ventricular ejection upon opening of the pulmonic valve 26), are indicative of changes in sympathetic tone. Specifically, a reduced pre-ejection period is indicative of an increase in sympathetic tone as a result of increased workload or emotional stress requiring increased cardiac output, which can be achieved by increasing the heart rate. Thus, pulmonary arterial pressure data can be correlated to the pre-ejection period, which can in turn be employed to control the heart rate to prevent, reduce or reverse increases in sympathetic tone. A reasonable relationship for determining pacing cycle length, and thus heart rate, is A times the pre-ejection period plus B. Constants A and B would be individually programmed for each patient and could be determined during a short period of exercise.

Returning to FIG. 9, the control module 42 is adapted to control the IMD 32 to adjust pacing cycle length based upon the relationship between the calculated pre-ejection period and a pre-programmed value or range representing a normal or desirable pre-ejection period. This pre-programmed value may be based upon historic diastolic pressure measurements. In one embodiment, if the pre-ejection period is below an acceptable pre-programmed value or range (block 250), the control module 42 instructs the IMD 32 to decrease the pacing cycle length, increasing the heart rate (block 252) until the pre-ejection period returns to an acceptable value or range in relation to the pre-programmed value.

A sudden step increase in the pre-ejection period may indicate a "loss of capture." Loss of capture occurs when the stimulating pulse delivered by a pacing device such as IMD 32 does not depolarize a sufficient volume of tissue to result in a "wave of activation" over the entire heart 20 to activate a cardiac contraction. This can happen if the electric field across the myocardial cell membrane in the myocardium closest to a pacing electrode is of insufficient strength to depolarize the cells.

If the patient is being paced in an atrial synchronous mode, as in CRT, (i.e., the device senses an atrial depolarization, waits for the duration of the programmed AV delay, and then paces the ventricle), then loss of capture will usually results in an increased pre-ejection period. However, if the patient is being paced in a single-chamber mode (indicating that the atrium is not sensed), then, since the intrinsic ventricular rhythm and the paced rhythm are totally asynchronous, a loss of capture will merely increase the variability within the pre-ejection period with some decreased and some increased values. In the first case, a sudden (i.e., from one heart-beat to the next) increase in pre-ejection period having a magnitude of either ten percent or more than two standard deviations from the previous mean value, would be sufficient to indicate loss of capture. In the second case, both an increase and a decrease in pre-ejection period of the same magnitude would indicate loss of capture.

In another embodiment, upon determining that a loss of capture has occurred based on the relationship between the pre-ejection period and a pre-programmed value representing previous pre-ejection periods, the IMD 32 increases pacing output until the previous or an appropriate pre-ejection period is regained. This indicates that the stimulating pulse delivered by the IMD 32 is depolarizing a sufficient volume of tissue to result in a "wave of activation" over the entire heart 20 to activate a cardiac contraction.

Figure 10:
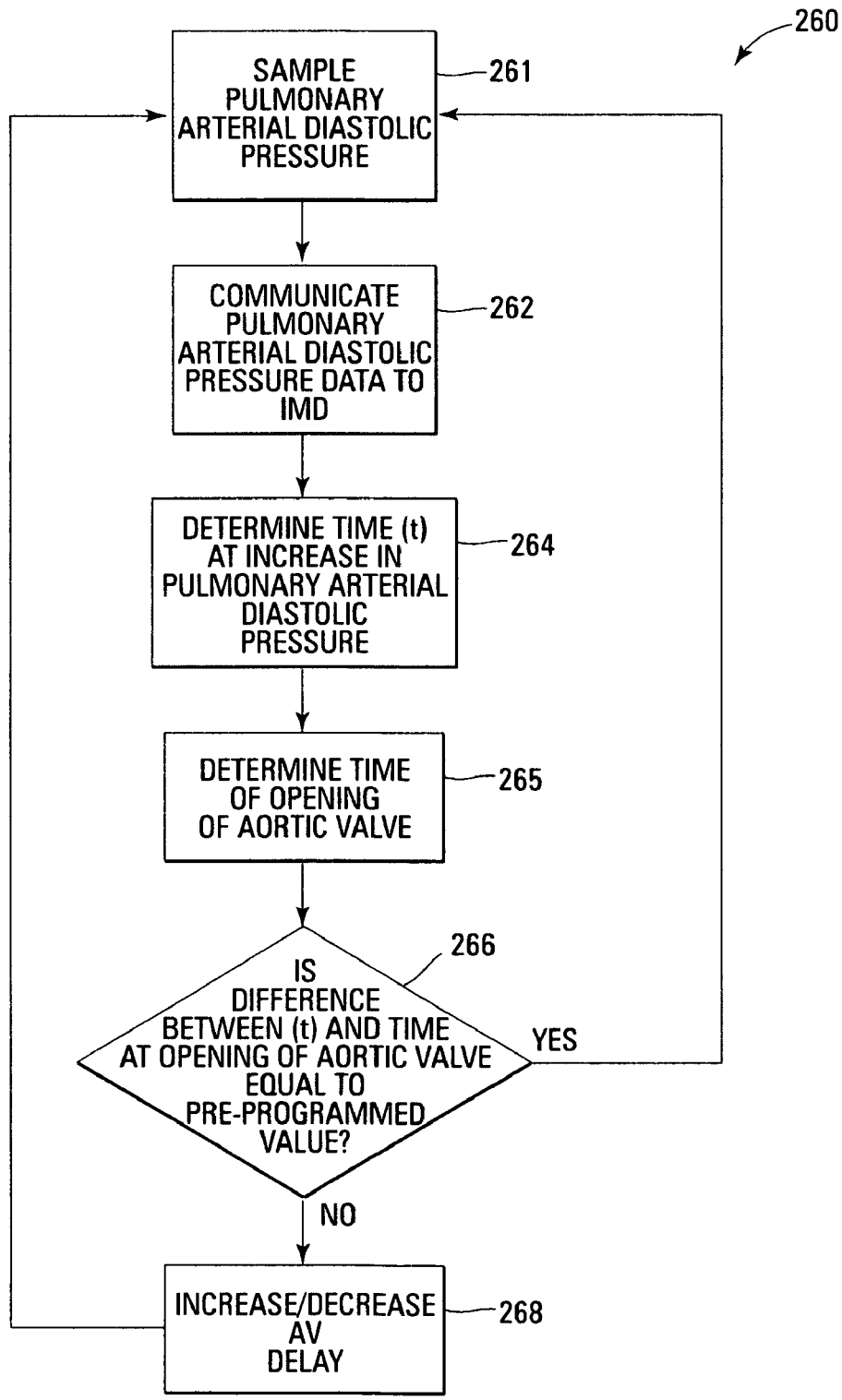
FIG. 10 is a flowchart illustrating a method of administering a therapeutic treatment to the heart in accordance with another embodiment of the present invention.

Another application of system 200 is shown in FIG. 10, a flowchart illustrating a method 260 of administering such a therapeutic treatment to the heart 20, in which the AV delay is adjusted so that the opening of the pulmonic valve 26, which is indicated by a sudden increase in pulmonary arterial pressure, is simultaneous with the opening of the aortic valve. Pulmonary arterial pressure is measured (block 261) and data is communicated to the IMD 232 (block 262). The timing of the pulmonic valve 26 is calculated from cyclical sudden increases in pulmonary arterial pressure (block 264). The timing of the beginning of the pressure increase in the pulmonary artery can also be determined by looking for a peak in the first derivative of the pulmonary arterial pressure waveform. The beginning of left ventricular ejection may be determined from a secondary sensor 235 adapted to sense left ventricular heart sounds, for example, S1, or the beginning of left ventricular volume decrease, which is measured by impedance across the left ventricle 30, or by the beginning of aortic or arterial flow determined by ultrasound or impedance or by a pressure sensor in the descending aorta or other artery (block 265).

Based upon the relationship between the calculated AV delay (based upon the diastolic pressure) and a pre-programmed value representing a normal or desirable AV delay, the control module 42 is adapted to control the output of the IMD 32. In one embodiment, the timing of the pulmonic valve and the timing of the aortic valve are compared (block 266) and if the difference is not equal to a pre-programmed value, the IMD 232 progressively lengthens or shortens the AV delay (block 268). This process may be repeated until the relationship between the diastolic pressure and the pre-programmed value is such that no further change in operating parameter is desired. In one embodiment, the process is repeated until the difference in time between the two events is minimized or reaches a pre-programmed value (block 266).

In another embodiment of the present invention, the system 10 is employed during follow-up care under physician guidance to optimize IMD operational programming. For example, the system 10 is employed to control AV delay or pacing site(s) in an IMD programming change to optimize right heart function during cardiac rhythm therapy by monitoring pulmonary arterial end diastolic pressure or pulmonary arterial pulse pressure. Virtually any change in therapy that decreases PADP that is above a pre-programmed value or range (approximately 15-20 mmHg), other than merely decreasing heart rate, is likely to be a good change, provided that pulse pressure does not simultaneously decrease. The impact of a programming change to the IMD 32 may be monitored over an extended time period (days or weeks) to determine whether the programming change was successful.

According to another embodiment, the pressure sensor unit 34 is also in communication with an external device. Such external devices may include monitoring, diagnostic or telemetry equipment. Such external equipment might also be in communication with the IMD 32 such that in addition to closed-loop control, a physician is able to monitor physiologic parameters of the pulmonary artery 22 and provide additional IMD operational inputs, such as programming changes.

A pulmonary arterial pressure sensor permits the real-time measurement of parameters related to important left heart parameters without actually being in the left ventricular blood volume. A sensor in the pulmonary artery 22 rather than the left ventricle 30 reduces the chance of thrombosis and permits accurate measurement of systolic intervals, such as pre-ejection period and ejection time, that are more difficult to estimate from the right ventricle 28. Further, the pulmonary artery 22 is more easily accessed and placement of the pulmonary sensor 34 is less likely to result in trauma to the heart 20 than placement in the left ventricle 30.

A significant benefit of the present invention is that through monitoring pressure in the pulmonary artery 22, the IMD 32 can discriminate lethal arrhythmias from those that are less dangerous, permitting the use of anti-tachy pacing protocols that may convert the rhythm without a large shock, thereby minimizing the risk of administrating painful shocks to conscious patients. This is done without resorting to sophisticated and inaccurate algorithms that attempt to make this discrimination based on the morphology of the intracardiac electrogram.

A system and method in accordance with the present invention may be employed to administer substantially any therapeutic treatment to the heart, as well as to monitor the performance and efficacy of implantable medical devices.

Figure 11:
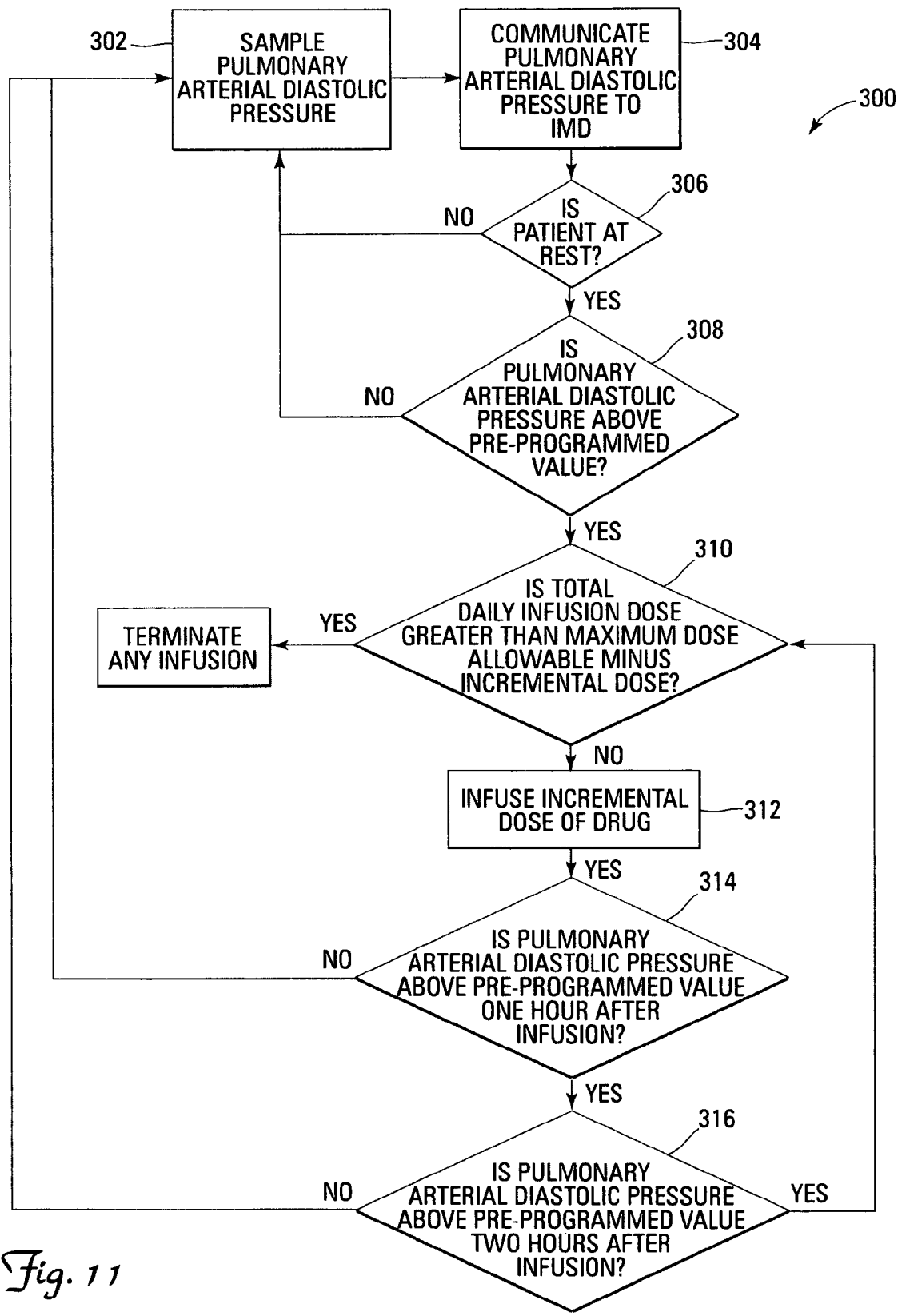
FIG. 11 is a flowchart illustrating a method of administering a therapeutic treatment to the heart in accordance with another embodiment of the present invention.

In one embodiment, IMD 32 is an implantable drug infusion device adapted for controlling delivery of a drug, such as a diuretic for reducing total fluid volume. The control module 42 may be adapted for controlling the volume and rate of drug delivery. FIG. 11 is a flowchart illustrating a method 300 for administering a drug such as furosemide, trade name Lasix™, for the treatment of decompensated heart failure, according to one embodiment of the present invention. The pressure sensor 34 takes pressure sensor readings (block 302) and communicates data representative of the pulmonary arterial diastolic pressure to the control module (block 304). Because blood pressure often increases during periods of activity, the PADP of a patient suffering from left ventricular dysfunction can increase from an average of 6-13 mmHG while at rest to an average of 20-30 mmHG when active. Thus, the control module 42 is adapted to first determine whether the patient is at rest or is active. This may be accomplished by monitoring activity levels with an accelerometer or by monitoring heart rate. Heart rate may be monitored with a separate sensor, or may be determined from the sensed pulmonary arterial pressure waveform.

When it is determined that the patient is at rest (block 306), the sensed PADP is compared to a pre-programmed value or threshold for desired PADP (block 308). The pre-programmed value can be chosen according to the patient's sex, height, weight and age, and according to historic PADP measurements. The control module 42 is adapted to instruct the IMD 32 to infuse drugs into the patient based upon the relationship between the diastolic pressure and the pre-programmed value. In one embodiment, if the resting PADP exceeds the pre-programmed value, infusion of the medication is commenced (block 312). Prior to infusing any drug, however, the control module 42 is adapted to determine whether the maximum daily dosage has been infused (block 310). If so, any further drug infusion is halted. The system 10 may continue to monitor PADP, may cease to monitor PADP and simply go into a resting mode, or may be provided with means to indicate the maximum daily dosage has been infused or to sound an alarm if the PADP remains above the threshold. In one embodiment, 80 mg of furosemide is infused. In one embodiment, the maximum dosage may be set at 800 mg of furosemide. Again, however, the maximum dosage varies depending on the patient's physical characteristics, medical history, and drug formula.

In one embodiment, approximately 80 mg of furosemide is infused at each infusion step, for a maximum daily dosage of 800 mg. However, the amount of medication or drug infused and the length of time over which it is infused will vary greatly depending on the patient's medical history, the formula and concentration of the drug being infused, and the difference between the sensed PADP and the pre-programmed value.

After a pre-determined period of time, for example, one hour, the PADP is again compared to the pre-programmed value (block 314). If the PADP has dropped below the pre-programmed value, then PADP is monitored on a regular basis thereafter. If, however, the PADP has not decreased below the pre-programmed value, the PADP is sampled again one hour later (block 316). Because the body tends to activate the renin-angiotensis-aldosterone system upon infusion, typically causing the PADP to increase to a peak approximately 30 minutes after infusion, the sampling delay following infusion helps to provide a more accurate representation of changes in PADP. Again, if the PADP had dropped below the pre-programmed value, then the PADP is monitored on a regular basis thereafter. If, however, the PADP has not decreased below the pre-programmed value, then a second volume of drug is infused (block 310).

This process may be repeated until the relationship between the diastolic pressure and the pre-programmed value is such that no further change in IMD operating parameter is desired. In one embodiment, the hourly sampling and bi-hourly infusing regime is continued until a maximum dosage has been achieved. The control module may be further provided with the ability to administer variable quantities of drug, variable rates of infusion, and variable concentrations of medication.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:

1. A method of administering a cardiac rhythm management therapy to the heart, the method comprising:
   sensing pulmonary arterial pressure from within the pulmonary artery with an implanted sensor;
   communicating data representative of the sensed pulmonary arterial pressure from the sensor to an implanted medical device;
   calculating a current pre-ejection period from the data;
   comparing the current pre-ejection period to a previously calculated pre-ejection period; and
   if the current pre-ejection period has changed compared to the previously calculated pre-ejection period, sending a cardiac rhythm management signal to adjust the heart rate, wherein one or more attributes of the cardiac rhythm management signal are based on a pre-programmed relationship between the current pre-ejection period and the cardiac cycle length; and
   repeating the process until the relationship between the current pre-ejection period and the previously calculated pre-ejection periods is such that no adjustment in the heart rate is necessary.

2. The method of claim 1 wherein determining if the pre-ejection period is changing includes determining if the pre-ejection period is increasing or decreasing, and adjusting the heart rate includes decreasing the heart rate if the pre-ejection period is increasing and increasing the heart rate if the pre-ejection period is decreasing.

3. The method of claim 1 wherein communicating data includes communicating data with one of acoustics, radio waves or ultra sound.

4. The method of claim 1 further comprising communicating the sensed pulmonary arterial pressure data to an external device.

5. A method of administering a cardiac rhythm management therapy to the heart, the method comprising:
   sensing pulmonary arterial diastolic pressure from within the pulmonary artery with an implanted sensor;
   communicating data representative of the sensed pulmonary arterial pressure from the sensor to an implanted medical device;
   comparing the pulmonary arterial diastolic pressure to a pre-programmed value; and
   limiting increases in the heart's pacing rate by sending a cardiac rhythm management signal to the heart to maintain pulmonary arterial diastolic pressure below the pre-programmed value; and repeating the process until the relationship between the pulmonary arterial diastolic pressure and the pre-programmed value is such that no adjustment is necessary.

6. The method of claim 5 wherein communicating data includes communicating data with one of acoustics, radio waves or ultra sound.

7. The method of claim 5 further comprising communicating the sensed pulmonary arterial pressure data to an external device.

8. A method of administering a therapeutic treatment to the heart, the method comprising:

sensing pulmonary arterial pressure from within the pulmonary artery with an implanted sensor;

communicating data representative of the sensed pulmonary arterial pressure from the sensor to an implanted medical device;

calculating heart rate and systolic and/or pulse pressure;

determining if, based on heart rate and systolic and/or pulse pressure, (1) a ventricular arrhythmia is occurring, and (2) if so, whether the ventricular arrhythmia is potentially lethal;

administering a defibrillation shock with the implantable medical device if a ventricular arrhythmia is occurring and is considered lethal; and administering an anti-tachy pacing protocol with the implantable medical device if a ventricular arrhythmia is occurring and is not considered lethal.

9. The method of claim 8 wherein communicating data includes communicating data with one of acoustics, radio waves or ultra sound.

10. The method of claim 8 further comprising communicating the sensed pulmonary arterial pressure data to an external device.

* * * * *